US009649317B2

(12) United States Patent
Ballatore et al.

(10) Patent No.: US 9,649,317 B2
(45) Date of Patent: May 16, 2017

(54) HETEROCYCLIC COMPOUNDS AND THEIR USE FOR THE TREATMENT OF NEURODEGENERATIVE TAUOPATHIES

(71) Applicant: The Trustees of The University of Pennsylvania, Philadelphia, PA (US)

(72) Inventors: Carlo Ballatore, Philadelphia, PA (US); Kurt R. Brunden, Media, PA (US); Adam T. Hoye, Philadelphia, PA (US); Virginia M. Y. Lee, Philadelphia, PA (US); Amos B. Smith, Merion, PA (US); John Q. Trojanowski, Philadelphia, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 19 days.

(21) Appl. No.: 14/429,101

(22) PCT Filed: Sep. 19, 2013

(86) PCT No.: PCT/US2013/060562
§ 371 (c)(1),
(2) Date: Mar. 18, 2015

(87) PCT Pub. No.: WO2014/047257
PCT Pub. Date: Mar. 27, 2014

(65) Prior Publication Data
US 2015/0224105 A1 Aug. 13, 2015

Related U.S. Application Data
(60) Provisional application No. 61/702,800, filed on Sep. 19, 2012.

(51) Int. Cl.
*A61K 31/5377* (2006.01)
*A61K 31/519* (2006.01)
*A61K 31/501* (2006.01)
*A61K 31/53* (2006.01)
*A61K 31/4985* (2006.01)
*A61K 31/50* (2006.01)
*A61K 31/506* (2006.01)

(52) U.S. Cl.
CPC ...... *A61K 31/5377* (2013.01); *A61K 31/4985* (2013.01); *A61K 31/50* (2013.01); *A61K 31/501* (2013.01); *A61K 31/506* (2013.01); *A61K 31/519* (2013.01); *A61K 31/53* (2013.01)

(58) Field of Classification Search
CPC .............. A61K 31/5377; A61K 31/506; A61K 31/519; A61K 31/50; A61K 31/4985; A61K 31/53; A61K 31/501
USPC .. 514/233.2, 243, 247, 249, 252.01, 255.05, 514/256, 259.31, 275
See application file for complete search history.

(56) References Cited

U.S. PATENT DOCUMENTS

| 5,986,135 A | 11/1999 | Pfrengle et al. |
|---|---|---|
| 6,117,876 A | 9/2000 | Pees et al. |
| 7,524,849 B2 | 4/2009 | Zhang et al. |
| 2003/0087888 A1 | 5/2003 | Regueiro-Ren |
| 2005/0124635 A1 | 6/2005 | Wu et al. |

FOREIGN PATENT DOCUMENTS

| WO | WO 2005/030775 A1 | 4/2005 |
|---|---|---|
| WO | WO 2005/117550 A2 | 12/2005 |
| WO | WO 2006-091728 | 8/2006 |
| WO | WO 2009/123486 A1 | 10/2009 |
| WO | WO 2011/037985 A1 | 3/2011 |

OTHER PUBLICATIONS

Ayral-Kaloustian et al., "Cevipabulin (TTI-237): Preclinical and Clinical Results for a Novel Antimicrotubule Agent", Methods and Findings in Experimental and Clinical Pharmacology, Sep. 2009, vol. 31, No. 7, 443-447.
Ballatore et al., "Microtubule stabilizing agents as potential treatment for Alzheimer's disease and related neurodegenerative tauopathies", Journal of Medicinal Chemistry, Nov. 2012, vol. 55, No. 21, 8979-8996.
Brunden et al., "Advances in tau-focused drug discovery for Alzheimer's disease and related tauopathies", Nature Reviews, Oct. 2009, vol. 8, 783-793.
Ballatore et al, "Discovery of Brain-Penetrant, Orally Bioavailable Aminothienopyridazine Inhibitors of Tau Aggregation", Journal of Medicinal Chemistry., May 9, 2010, 53, 3739-3747.
Ballatore et al, "Mediated Neurodegeneration in Alzheimer's Disease and Related Disorders", Nature Reviews, Neuroscience, Sep. 2007, 8, 663-672.
Beyer et al, "TTI-237: A Novel Microtubule-Active Compound With In Vivo Antitumor Activity", Cancer Research, Apr. 1, 2008, 68, 2292-2300.
Black et al, "Dynamics of Alpha-Tubulin Deacetylation in Intact Neurons", Journal of Neuroscience, Jan. 1, 1989, 9(1), 358-368.
Brunden et al, "Brain-Penetrant Microtubule-Stabilizing Compounds As Potential Therapeutic Agents For Tauopathies", Biochem. Soc. Trans., 2012, 40, 661-666.
Brunden et al, "The Characterization of Microtubule-Stabilizing Drugs as Possible Therapeutic Agents for Alzheimer's Disease and Related Tauopathies", Pharmacological Research, Apr. 2011 63(4), 341-351.

(Continued)

*Primary Examiner* — Jennifer M Kim
(74) *Attorney, Agent, or Firm* — Baker & Hostetler LLP

(57) ABSTRACT

The present invention is directed to triazolopyrimidine, phenylpyrimidine, pyridopyridazine, and pyridotriazine compounds which are microtubule-stabilizing compounds and their use in the treatment of neurodegenerative disorders, in particular, tauopathies, such as for example, Alzheimer's disease, frontotemporal lobar degeneration, Pick's disease, progressive supranuclear palsy (PSP), and corticobasal degeneration. In addition, the compounds of the invention may be useful for other diseases where tau pathology is a comorbidity or where microtubule function is compromised, for example, schizophrenia, Parkinson's disease (PD), PD with dementia, Lewy body disease with dementia, and amyotrophic lateral sclerosis.

32 Claims, 14 Drawing Sheets

(56) References Cited

OTHER PUBLICATIONS

Brunden et al., Epothilone D Improves Microtubule Density, Axonal Integrity and Cognition in a Transgenic Mouse Model of Tauopathy, Journal. Neuroscience, Oct. 13, 2010, 30(41), 13861-13866.

Buee et al, "Tau Protein Isoforms, Phosphorylation and Role in Neurodegenerative Disorders", Brain Research Reviews, Aug. 2000, 33(1), 95-130.

Crowley et al. "Neimentowski-type Synthesis of Pyrido[3,2-e][1,2,4]Trazines: Potent Aza-Analogs of.Pyrido[2,3-b]pyrazine Fungicides", Tetrahedron Letters, May 12, 2010, 51(19), 2652-2654.

Crowley et al. "Synthesis and Fungicidal Activity Oftubulin Polymerisation Promoters. Part 1: Pyrido[2,3-b]pyrazines", Pest Management Science, Feb. 2010, 66(2), 178-185.

Farah et al, "Altered Levels and Distribution of Microtubule-Associated Proteins Before Disease Onset in a Mouse Model of Amyotrophic Lateral Sclerosis", Journal of Neurochemistry, Jan. 2003, 84(1), 77-86.

International Application No. PCT/US2013/60562: International Search Report and the Written Opinion dated Apr. 10, 2014.

Laferriere et al, "Synthesis and Assembly in Differentiating Neurons", Biochemistry and Cell Biology, Feb. 1997, 75(2), 103-117.

Lamberth et al. "Synthesis and Fungicidal Activity of Tubulin Polymerisation Promoters. Part 2: Pyridazines", May 1, 2012, Bioorganic Medicinal Chemistry, 20(9), 2803-2810.

Lei et al, "Tau Protein: Relevance to Parkinson's Disease", The International Journal of Biochemistry & Cell Biology, 42(11), Nov. 2010, 1775-1778.

Petratos et al, "Novel Therapeutic Targets for Axonal Degeneration in Multiple Sclerosis", Journal of Neuropathology, Experimental Neurology, Apr. 2010, 69(4), 323-334.

PubChem-CID 11655014, Create Date: Oct. 27, 2006, 3 pages, Https://pubchem.ncbi.nlm.nih.gov/summary/summary.cgi?cid=11655014.

Roy et al, "Axonal Transport Defects: A Common Theme in Neurodegenerative Diseases", Acta Neuropathology, (Berl),.Jan. 12, 2005, 109(1), 5-13.

Schmidt et al, "Tau Isoform Profile and Phosphorylation State in Dementia Pugilistica Recapitulate Alzheimer's Disease", Acta Neuropathology, Mar. 2001, 101, 518-524.

Shively et al, "Dementia Resulting From Traumatic Brain Injury", Arch Neurology., Jul. 9, 2012, 69(10), 1245-1251.

Smith et al, "Protein Accumulation in Traumatic Brain Injury", NeuroMolecular Medicine, Oct. 2003, 4(1), 59-72.

Yoshiyama, "Enhanced Neurofibrillary Tangle Formation, Cerebral Atrophy, and Cognitive Deficits Induced by Repetitive Mild Brain Injury in a Transgenic Tauopathy Mouse Model", Journal of Neurotrauma, Oct. 2005, 22(10), 1134-1141.

Zhang et al, "Synthesis and SAR of [1,2,4]triazolo[1,5-a]pyrimidines, A Class of Anticancer Agents With a Unique Mechanism of Tubulin Inhibition" 2007, Journal of Medicinal Chemistry, 50(2),319-327.

Zhang et al, "Synthesis and SAR of 6-chloro-4-Fluoroalkylamino-2-Heteroaryl-5-(substituted)Phenylpyrimidines As Anti-Cancer Agents", Bioorganic & Medicinal Chemistry, Jan. 1, 2009, 17(1), 111-118.

Zhang et al. "The Microtubule-Stabilizing Agent, Epothilone D, Reduces Axonal Dysfunction, Cognitive Deficits, Neurotoxicity and Alzheimer-Like Pathology in an Interventional Study With Aged Tau Transgenic Mice", Mar. 14, 2012, The Journal of. Neuroscience, 32(11), 3601-3611.

Zhang,B. et al. "Microtubule-Binding Drugs Offset Tau Sequestration by Stabilizing Microtubules and Reversing Fast Axonal Transport Deficits in a Tauopathy Model", Proc. National Academy of Sciences U S A, Jan. 4, 2005,102(1), 227-231.

51554

51555

51556

51561

51562

HETEROCYCLIC COMPOUNDS AND THEIR USE FOR THE TREATMENT OF NEURODEGENERATIVE TAUOPATHIES

CROSS-REFERENCE TO RELATED APPLICATIONS

This application is the National Stage Entry of International Application No. PCT/US2013/060562, filed Sep. 19, 2013, which claims the benefit of and priority to U.S. Provisional Application No. 61/702,800, filed Sep. 19, 2012, the entire disclosures of which are incorporated herein by reference for any and all purposes.

GOVERNMENT RIGHTS

This invention was made with government support under grant numbers R01 AG044332 and AG0344140 awarded by the National Institutes of Health. The government has certain rights in the invention.

TECHNICAL FIELD

The invention is directed to compounds and methods for the treatment of neurodegenerative tauopathies such as Alzheimer's disease and frontotemporal lobar degeneration.

BACKGROUND

Neurodegenerative tauopathies, including Alzheimer's disease (AD), are characterized by the misfolding and aggregation of the microtubule (MT)-associated protein tau. Normally, tau binds to and stabilizes MTs, thereby maintaining the network of MTs essential for axonal transport in neurons. In AD, tau becomes sequestered into aggregates, known as neurofibrillary tangles (NFTs) and neuropil threads, resulting in reduced MT-binding. This loss of tau function is believed to lead to MT destabilization and consequent axonal transport deficits, which could result in neuronal dysfunction and death.

Other neurodegenerative diseases where MT function may be compromised include frontotemporal lobar degeneration, multiple sclerosis, Parkinson's disease, amyotrophic lateral sclerosis, schizophrenia, Huntington's disease, multiple sclerosis, and traumatic brain injury (TBI), especially repetitive TBI (rTBI) such as that due to dementia pugilistica and recurrent football concussions and military closed head injuries, which also is known as chronic traumatic encephalopathy (CTE).

Compounds that can cross the blood brain barrier and effectively stabilize MT are needed in order to treat neurodegenerative diseases caused, at least in part, by misfolding and aggregation of the MT-associated protein tau.

SUMMARY

Triazolopyrimidine compounds of formula I, phenylpyrimidine compounds of formula II, pyridopyridazine and pyridotriazine compounds of formula III, and pyridazine compounds of formula IV, as described herein, are described as being useful for the treatment of neurodegenerative diseases.

DETAILED DESCRIPTION OF ILLUSTRATIVE EMBODIMENTS

Figure 1:
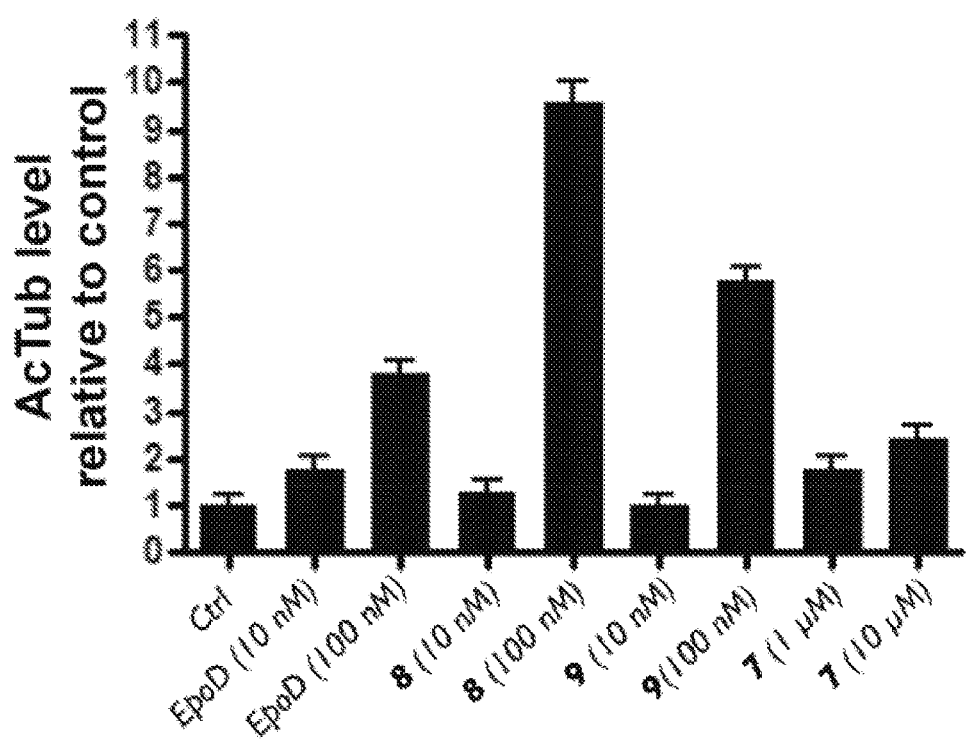
FIG. 1 depicts MT-stabilization assay (acetyl tubulin, "AcTub") results of embodiments of the invention in HEK/QBI 293 cells.
Figure 2:
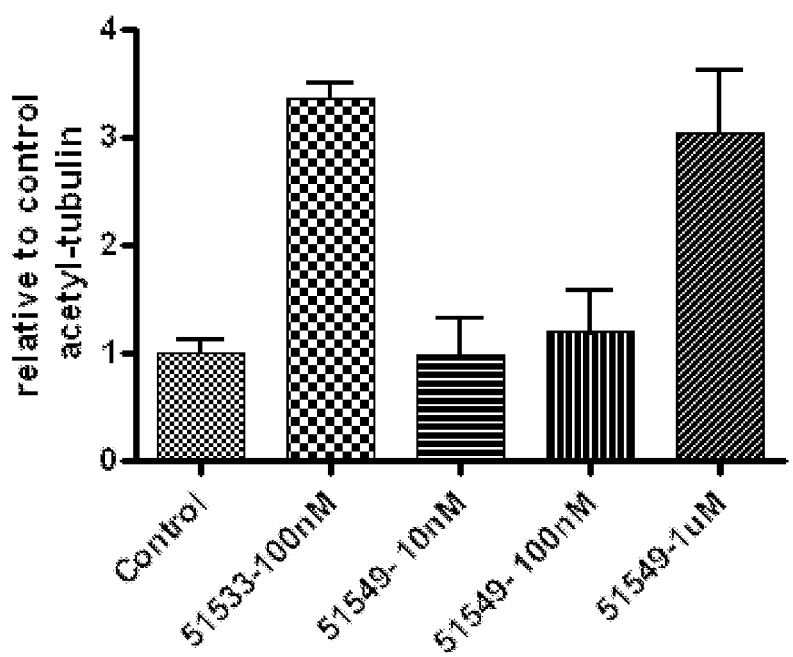
FIG. 2 depicts acetyl-tubulin level in QBI cells after 4 hours of treatment with one preferred compound of the invention (CNDR-51549).
Figure 3:
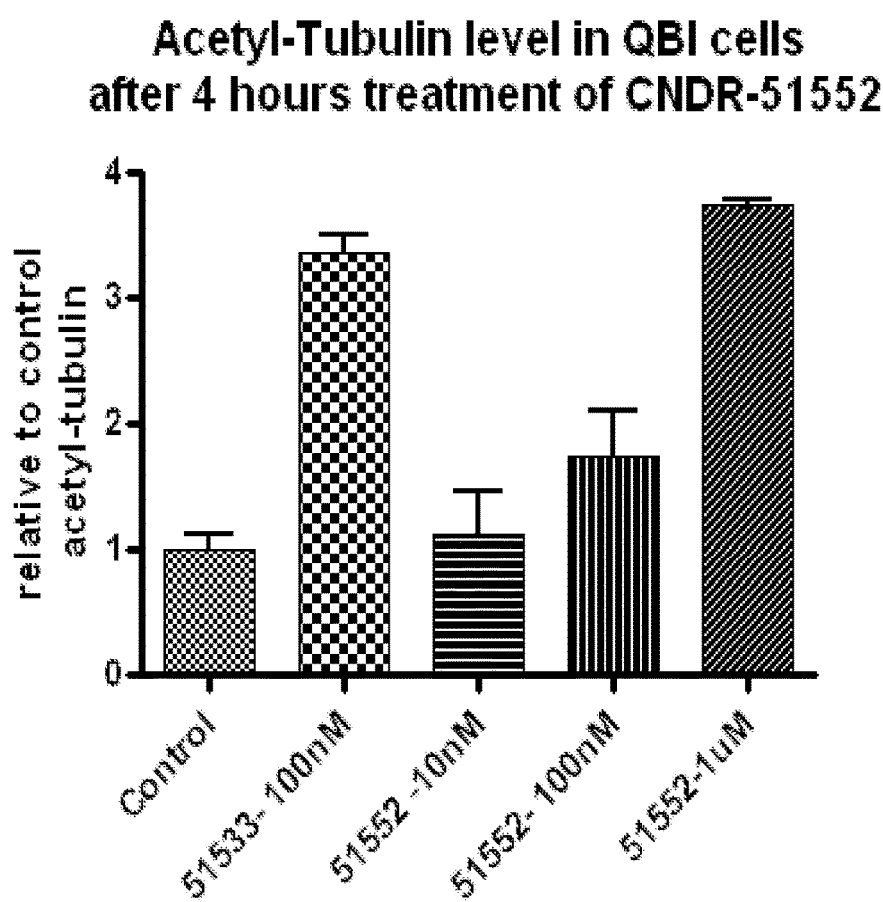
FIG. 3 depicts acetyl-tubulin level in QBI cells after 4 hours of treatment with one preferred compound of the invention (CNDR-51552).
Figure 4:
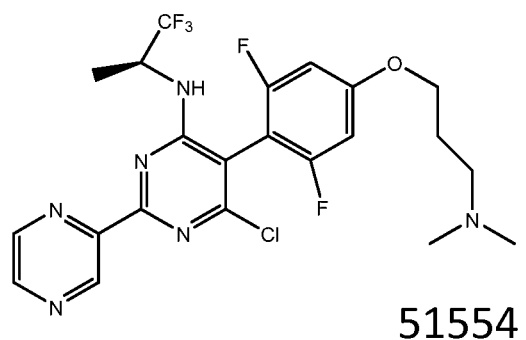
FIG. 4 depicts acetyl-tubulin level in QBI cells after 4 hours of treatment with one preferred compound of the invention (CNDR-51554).
Figure 4:
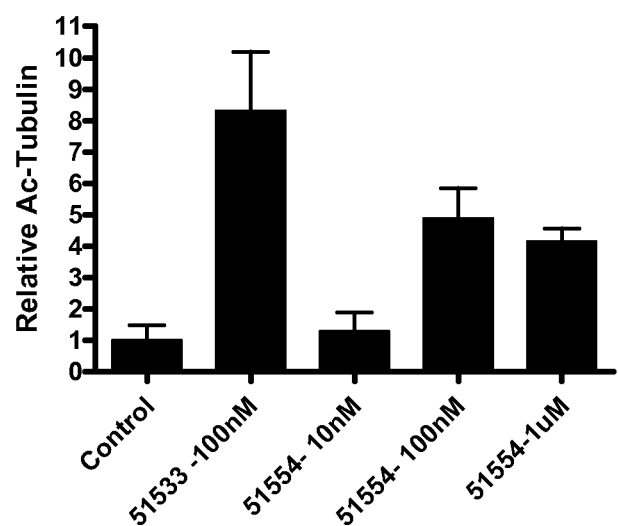
Figure 5:
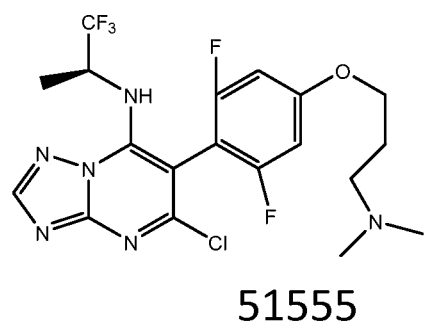
FIG. 5 depicts acetyl-tubulin level in QBI cells after 4 hours of treatment with one preferred compound of the invention (CNDR-51555).
Figure 5:
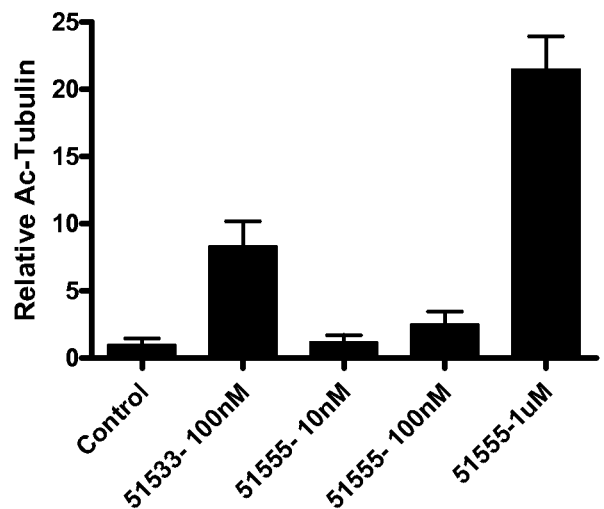
Figure 6:
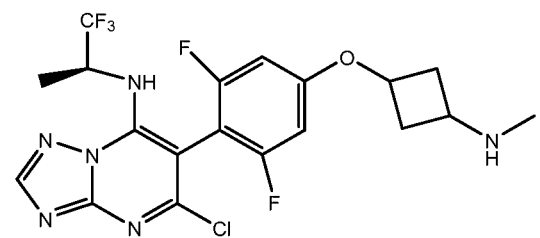
FIG. 6 depicts acetyl-tubulin level in QBI cells after 4 hours of treatment with one preferred compound of the invention (CNDR-51556).
Figure 6:
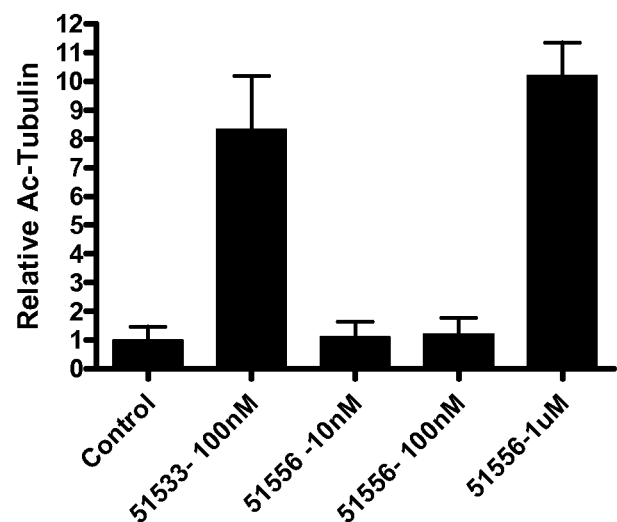
Figure 7:
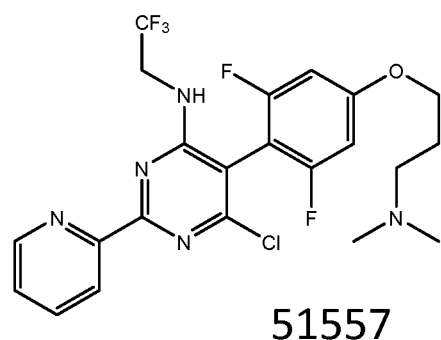
FIG. 7 depicts acetyl-tubulin level in QBI cells after 4 hours of treatment with one preferred compound of the invention (CNDR-51557).
Figure 7:
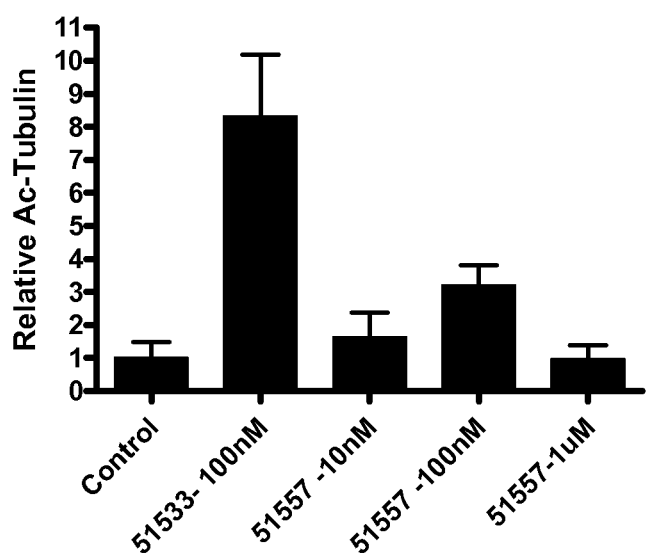
Figure 8:
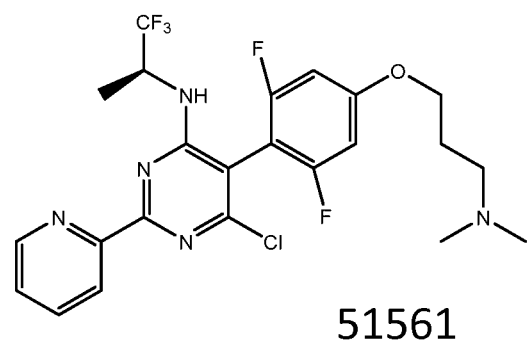
FIG. 8 depicts acetyl-tubulin level in QBI cells after 4 hours of treatment with one preferred compound of the invention (CNDR-51561).
Figure 8:
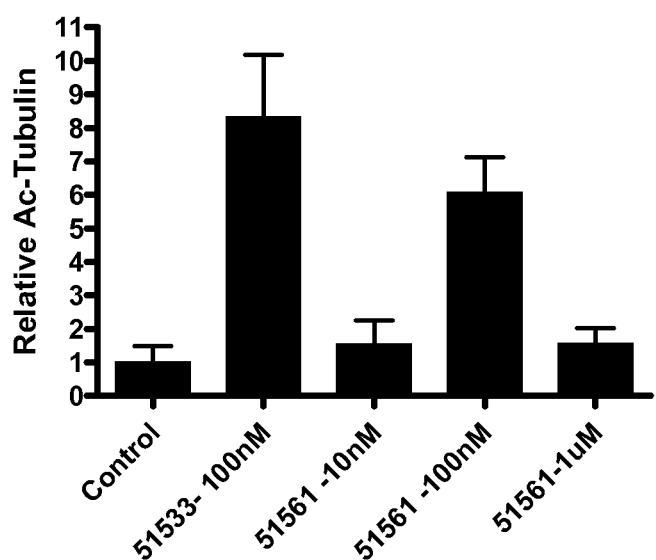
Figure 9:
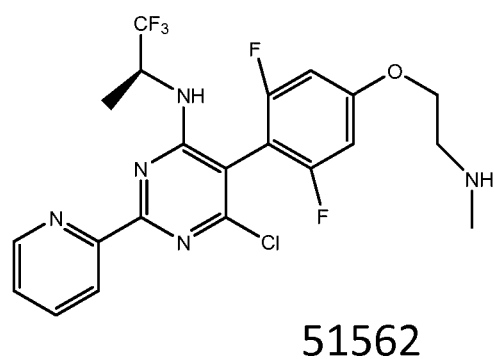
FIG. 9 depicts acetyl-tubulin level in QBI cells after 4 hours of treatment with one preferred compound of the invention (CNDR-51562).
Figure 9:
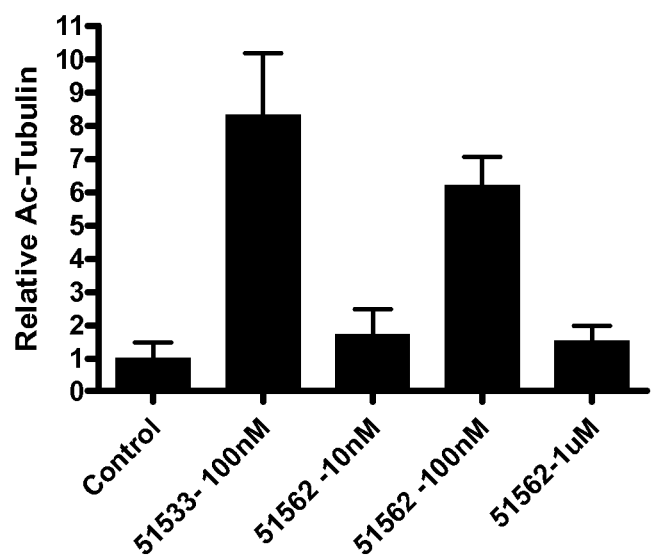
Figure 10:
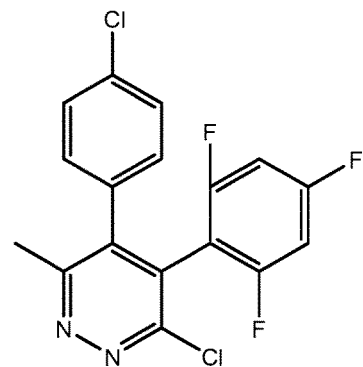
FIG. 10 depicts acetyl-tubulin level in QBI cells after 4 hours of treatment with one preferred compound of the invention (CNDR-51565).
Figure 10:
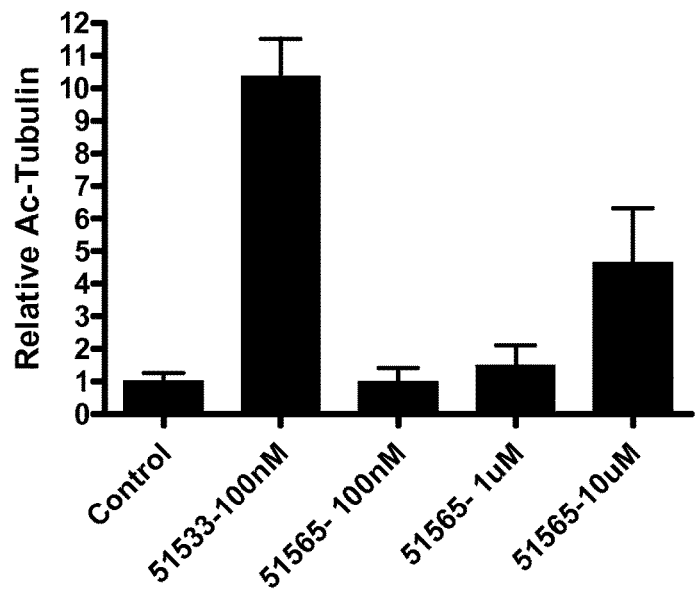
Figure 11:
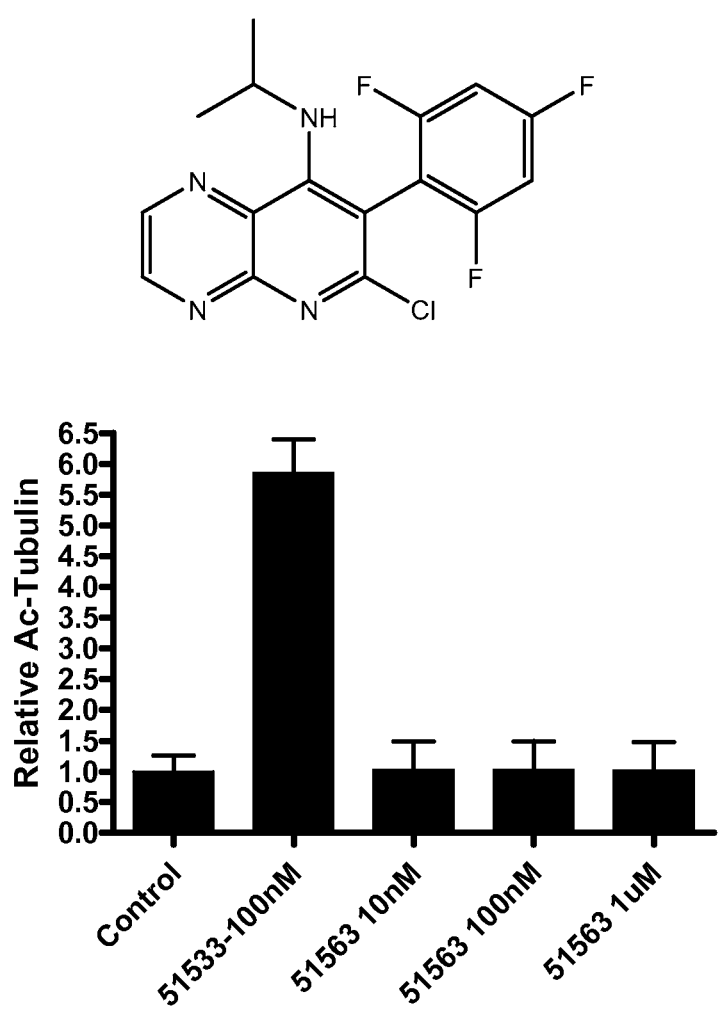
FIG. 11 depicts acetyl-tubulin level in QBI cells after 4 hours of treatment with one preferred compound of the invention (CNDR-51563).
Figure 12:
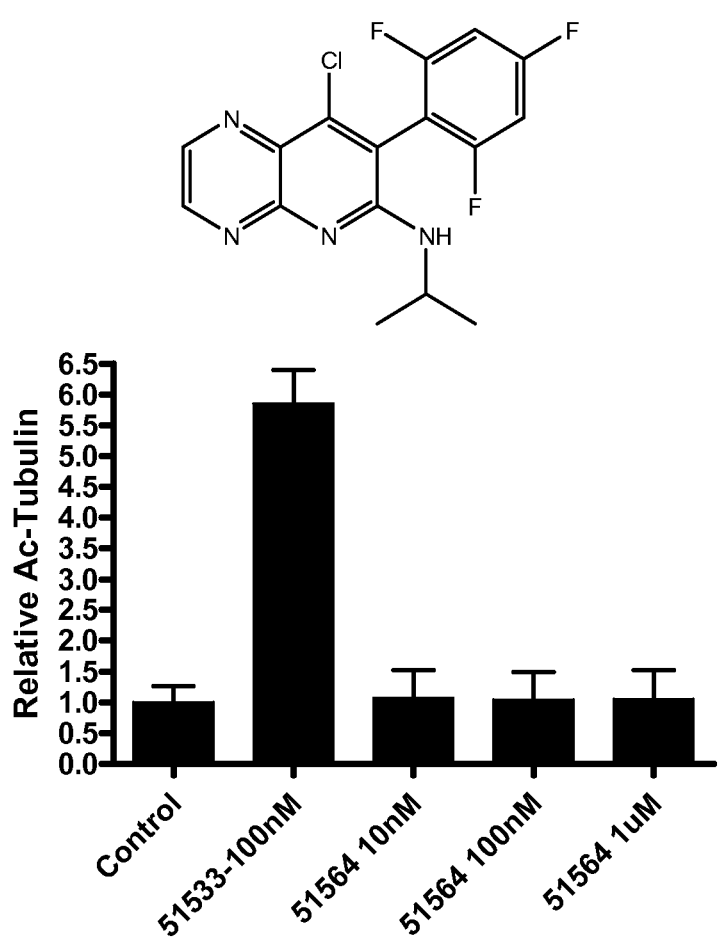
FIG. 12 depicts acetyl-tubulin level in QBI cells after 4 hours of treatment with one preferred compound of the invention (CNDR-51564).

It has now been discovered that certain classes of microtubule-stabilizing compounds will be useful in treating neurodegenerative diseases, in particular, tauopathies, for example, Alzheimer's disease, frontotemporal lobar degeneration, Pick's disease, progressive supranuclear palsy (PSP), and corticobasal degeneration. In addition, the compounds of the invention may be useful for other diseases where tau pathology is a co-morbidity or where microtubule function is compromised, for example, schizophrenia, Parkinson's disease (PD), PD with dementia, Lewy body disease with dementia, and amyotrophic lateral sclerosis.

The compounds of the invention can also be used to treat traumatic brain injury (TBI), especially repetitive TBI (rTBI), such as that due to dementia pugilistica and recurrent football concussions and military closed head injuries such as that due to IEDs, which also is known as chronic traumatic encephalopathy (CTE), with features of tauopathy or AD-like pathology. It is speculated that CTE also may emerge from PTSD.

These classes of compounds include triazolopyrimidine compounds of formula I and phenylpyrimidine compounds of formula II, as described herein. Other classes of compounds for use in the invention include pyridopyridazine and pyridotriazine compounds of formula III and pyridazine compounds of formula IV, as described herein.

Certain of the compounds described herein, that is, compounds of formulas I, II, III, and IV, have been previously studied for their anti-fungal and anti-cancer properties. As described herein, the compounds of formulas I, II, III, and IV are also useful in the treatment of neurodegenerative diseases.

Phenylpyrimidine compounds for use in the invention include those of formula I:

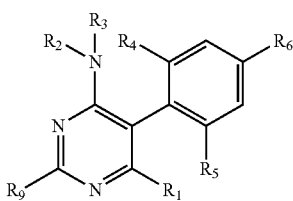

wherein $R_1$ is H, Cl, F, or Br;
$R_2$ is $C_{1-6}$alkyl or substituted $C_{1-6}$alkyl;
$R_3$ is H; or $R_2$ and $R_3$, together with the N atom to which they are attached, form a heterocyclo$C_{2-6}$alkyl;
$R_4$ is H, Cl, F, or Br;
$R_5$ is H, Cl, F, or Br;
$R_6$ is F, Cl, Br, —$N_3$, —$OC_{1-6}$alkyl; —$OC_{1-6}$alkyleneNR$_7$R$_8$, wherein $R_7$ and $R_8$ are each independently H or $C_{1-6}$alkyl; and
$R_9$ is pyridinyl, pyrimidyl, pyrazinyl, imidazolyl, pyrrolyl, pyrazolyl, quinolinyl, isoquinolinyl, thienyl, or furyl, each of which may be optionally substituted with one or more of F, Cl, Br, or $C_{1-6}$alkyl.

Stereoisomeric forms of the compounds of formula I, for example, enantiomers, diastereomers, and atropisomers, are also within the scope of the invention, as are pharmaceutically acceptable salts of any compound or stereoisomer of formula I.

Particularly preferred compounds of formula I include those wherein $R_1$ is Cl. In other embodiments, $R_1$ is H. In yet others, $R_1$ is F. In still other embodiments, $R_1$ is Br.

Preferably, in compounds of formula I, $R_3$ is H. In such embodiments, $R_2$ is $C_{1-6}$alkyl, for example, methyl, ethyl, propyl, isopropyl, butyl, sec-butyl, and tert-butyl. Also in embodiments wherein $R_3$ is H, $R_2$ is substituted $C_{1-6}$alkyl, wherein the alkyl is substituted with, for example halogen or trihaloalkyl such as trifluoromethyl. $R_2$ is preferably —CH(CH$_3$)CF$_3$, and all stereoisomers thereof, or —CH$_2$CF$_3$.

In alternative embodiments, $R_2$ and $R_3$, together with the N atom to which they are attached, form a heterocyclo-$C_{3-6}$alkyl, for example, a piperdinyl, piperazinyl, or morpholinyl. Such heterocyclo$C_{3-6}$alkyls can also be optionally substituted with, for example, one or more $C_{1-6}$alkyl, for example, methyl, ethyl, propyl, isopropyl, butyl, sec-butyl, and tert-butyl.

In the invention, $R_4$ is H, Cl, F, or Br. In some embodiments, $R_4$ is H. In other embodiments, $R_4$ is Cl. In yet other embodiments, $R_4$ is F. In yet other embodiments, $R_4$ is Br.

In the invention, $R_5$ is H, Cl, F, or Br. In some embodiments, $R_5$ is H. In other embodiments, $R_5$ is Cl. In yet other embodiments, $R_5$ is F. In yet other embodiments, $R_5$ is Br.

Particularly preferred compounds include those wherein $R_4$ and $R_5$ are each F.

In the invention, $R_6$ is F, Cl, Br, —$OC_{1-6}$alkyl; or —$OC_{1-6}$alkyleneNR$_7$R$_8$, wherein $R_7$ and $R_8$ are each independently H or $C_{1-6}$alkyl. $R_7$ and $R_8$ can be the same or different. In some preferred embodiments, $R_6$ is F. In some preferred embodiments, $R_6$ is Cl. In some preferred embodiments, $R_6$ is Br. In some embodiments, $R_6$ is —$N_3$. In other embodiments, $R_6$ is —$OC_{1-6}$alkyl, wherein the $C_{1-6}$alkyl is, for example, methyl, ethyl, propyl, isopropyl, butyl, sec-butyl, and tert-butyl. In yet other embodiments, $R_6$ is —$OC_{1-6}$alkyleneNR$_7$R$_8$, wherein $R_7$ and $R_8$ are each independently H or $C_{1-6}$alkyl, for example, methyl, ethyl, propyl, and the like. Preferred alkylene moieties include those having 1, 2, 3, 4, 5, or 6 carbon atoms. Particularly preferred compounds are those wherein $R_6$ is —O—CH$_2$CH$_2$CH$_2$—N(CH$_3$)$_2$. In other embodiments, $R_6$ is —O—CH$_2$CH$_2$CH$_2$—NH(CH$_3$).

In other preferred compounds of formula I, $R_4$, $R_5$, and $R_6$ are each F.

In preferred embodiments, $R_9$ is pyridinyl, preferably 2-pyridinyl, pyrazinyl, preferably 2-pyrazinyl, or pyrazolyl, preferably 1-pyrazolyl, any of which can be substituted with one or more of F, Cl, Br, or $C_{1-6}$alkyl, for example, methyl, ethyl, propyl, butyl, and the like. In other embodiments, R9 is pyrimidyl, imidazolyl, pyrrolyl, quinolinyl, isoquinolinyl, thienyl, or furyl, any of which can be substituted with one or more of F, Cl, Br, or $C_{1-6}$alkyl, for example, methyl, ethyl, propyl, butyl, and the like.

Particularly preferred compounds of formula I, include, for example, the compounds set forth in the following Table 1:

TABLE 1

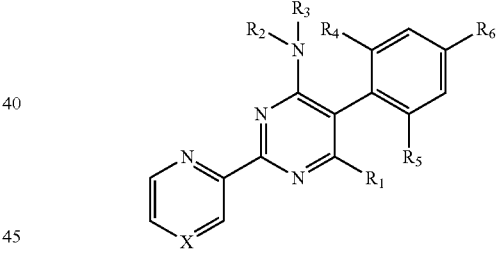

| X | $R_1$ | $R_2$ | $R_3$ | $R_4$ | $R_5$ | $R_6$ |
|---|---|---|---|---|---|---|
| N | Cl | —CH(CH$_3$)CF$_3$ (S) | H | F | F | F |
| N | Cl | —CH(CH$_3$)CF$_3$ (R) | H | F | F | F |
| N | Cl | —CH(CH$_3$)CF$_3$ (S,R) | H | F | F | F |
| N | Cl | H | H | F | F | F |
| CH | Cl | —CH(CH$_3$)CF$_3$ (S) | H | F | F | F |
| CH | Cl | —CH(CH$_3$)CF$_3$ (R) | H | F | F | F |
| CH | Cl | —CH(CH$_3$)CF$_3$ (S,R) | H | F | F | F |
| CH | Cl | H | H | F | F | F |
| N | Cl | —CH(CH$_3$)CF$_3$ (S) | H | F | F | —OCH$_2$CH$_2$CH$_2$N(CH$_3$)$_2$ |
| N | Cl | —CH(CH$_3$)CF$_3$ (R) | H | F | F | —OCH$_2$CH$_2$CH$_2$N(CH$_3$)$_2$ |
| N | Cl | —CH(CH$_3$)CF$_3$ (S,R) | H | F | F | —OCH$_2$CH$_2$CH$_2$N(CH$_3$)$_2$ |
| CH | Cl | H | H | F | F | —OCH$_2$CH$_2$CH$_2$N(CH$_3$)$_2$ |
| CH | Cl | H | H | F | F | —OtBu |
| CH | Cl | —CH(CH$_3$)CF$_3$ (S) | H | F | F | —OCH$_2$CH$_2$CH$_2$N(CH$_3$)$_2$ |
| CH | Cl | —CH(CH$_3$)CF$_3$ (S) | H | F | F | —OCH$_2$CH$_2$CH$_2$NH(CH$_3$) |

Other preferred compounds of formula I include:

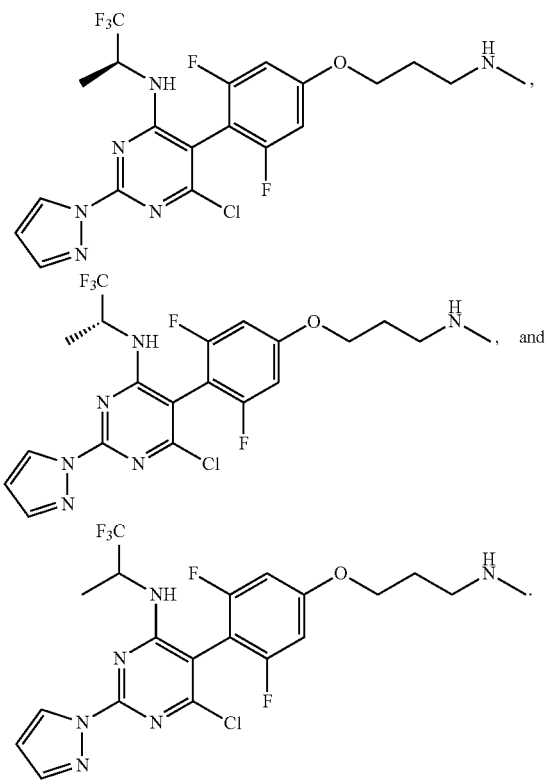

Triazolopyrimidine compounds for use in the invention include those of formula II:

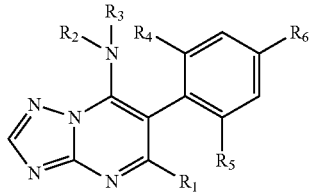

wherein
$R_1$ is H, Cl, F, or Br;
$R_2$ is $C_{1-6}$alkyl, or substituted $C_{1-6}$alkyl;
$R_3$ is H; or $R_2$ and $R_3$, together with the N atom to which they are attached, form a heterocyclo$C_{3-6}$alkyl;
$R_4$ is H, Cl, F, or Br;
$R_5$ is H, Cl, F, or Br;
$R_6$ is F, Cl, Br, —$N_3$, —$OC_{1-6}$alkyl; —$OC_{1-6}$alkyleneOH;
—$OC_{1-6}$alkylene-halo;
—$OC_{1-6}$alkyleneNR$_7$R$_8$; —$OC_{1-6}$substituted-alkyleneNR$_7$R$_8$; or
—$OC_{3-6}$cycloalkyleneNR$_7$R$_8$, wherein $R_7$ and $R_8$ are each independently H,
$C_{1-6}$alkyl, substituted $C_{1-6}$alkyl, —C(O)$C_{1-6}$alkyl, or aryl; or $R_7$ and $R_8$ together form a heterocyclic ring.
Some embodiments of the invention include compounds of formula II wherein
$R_1$ is H, Cl, F, or Br;
$R_2$ is $C_{1-6}$alkyl, or substituted $C_{1-6}$alkyl;
$R_3$ is H; or $R_2$ and $R_3$, together with the N atom to which they are attached, form a heterocyclo$C_{3-6}$alkyl;
$R_4$ is H, Cl, F, or Br;
$R_5$ is H, Cl, F, or Br;
$R_6$ is F, Cl, Br, —$OC_{1-6}$alkyl; —$OC_{1-6}$alkyleneNR$_7$R$_8$, or —$OC_{3-6}$cycloalkyleneNR$_7$R$_8$, wherein $R_7$ and $R_8$ are each independently H or $C_{1-6}$alkyl.

Stereoisomeric forms of the compounds of formula II, for example, enantiomers, diastereomers, and atropisomers, are also within the scope of the invention, as are pharmaceutically acceptable salts of any compound or stereoisomer of formula II.

Preferred compounds of formula II include those wherein $R_1$ is Cl. Other preferred compounds of formula II include those wherein $R_1$ is H. Other preferred compounds of formula II include those wherein $R_1$ is F. Other preferred compounds of formula II include those wherein $R_1$ is Br.

Exemplary compound of formula II include those wherein $R_2$ is $C_{1-6}$alkyl, for example, methyl, ethyl, propyl, isopropyl, butyl, sec-butyl, and tert-butyl. Also preferred are compounds of formula II wherein $R_2$ is substituted $C_{1-6}$alkyl, wherein the alkyl is substituted with halogen or trihaloalkyl such as trifluoromethyl. For example, $R_2$ is preferably —CH(CH$_3$)(CF$_3$), and all stereoisomers thereof, and —CH$_2$(CF$_3$).

In some embodiments, $R_2$ and $R_3$, together with the nitrogen atom to which they are attached, form a heterocyclo$C_{3-6}$alkyl, such as, for example, morpholinyl, piperidinyl, and piperazinyl.

In preferred embodiments of compounds of formula II of the invention $R_3$ is H.

In some embodiments, $R_4$ is H. Preferably $R_4$ is F. In other embodiments, $R_4$ is Cl. In other embodiments, $R_4$ is Br.

In some embodiments, $R_5$ is H. Preferably $R_5$ is F. In other embodiments, $R_5$ is Cl. In other embodiments, $R_5$ is Br.

In particularly preferred embodiments of the invention, $R_3$, $R_4$, and $R_5$ are each F.

Also preferred are compounds of formula II wherein $R_6$ is F. Other preferred compounds of formula II are those wherein $R_6$ is Cl. Other preferred compounds of formula II are those wherein $R_6$ is Br. IN other embodiments, $R_6$ is —$N_3$. Other preferred compounds of formula II are those wherein $R_6$ is H. It is particularly preferred that $R_6$ is F when $R_3$, $R_4$, and $R_5$ are each F.

In some embodiments, $R_6$ is —$OC_{1-6}$alkyl wherein preferred alkyl groups are methyl, ethyl, propyl, isopropyl, butyl, sec-butyl, and t-butyl.

In yet other embodiment, $R_6$ is —$OC_{1-6}$alkyleneOH wherein the $C_{1-6}$alkylene includes 1, 2, 3, 4, 5, or 6 carbons. Preferably, the alkylene is —CH$_2$CH$_2$CH$_2$—.

In yet other embodiment, $R_6$ is —$OC_{1-6}$alkylene-halo wherein the $C_{1-6}$alkylene includes 1, 2, 3, 4, 5, or 6 carbons. Preferably, the alkylene is —CH$_2$CH$_2$CH$_2$— and the halo is preferably F or Cl.

In other preferred embodiments, $R_6$ is —$OC_{1-6}$alkyleneNR$_7$R$_8$, wherein the $C_{1-6}$alkylene wherein the $C_{1-6}$alkylene includes 1, 2, 3, 4, 5, or 6 carbons. Preferably, the alkylene is —CH$_2$CH$_2$CH$_2$—.

Particularly preferred embodiments of —$OC_{1-6}$alkyleneNR$_7$R$_8$ include, for example, —O—CH$_2$CH$_2$CH$_2$—N(CH$_3$)$_2$ or —O—CH$_2$CH$_2$CH$_2$—NH(CH$_3$). It is particularly preferred that $R_6$ is —$OC_{1-6}$alkyleneNR$_7$R$_8$ when $R_3$, $R_4$, and $R_5$ are each F.

In other embodiments, $R_6$ is —$OC_{1-6}$substituted-alkyleneNR$_7$R$_8$, wherein the $C_{1-6}$alkylene includes 1, 2, 3, 4, 5, or 6 carbons. Preferably, the alkylene is a $C_3$alkylene. Preferred substitutents include halogen, $C_{1-6}$alkyl, and heterocycloalkyl. $R_7$ and $R_8$ can be the same or different. Preferably, $R_7$ and $R_8$ are independently H or methyl. Particularly preferred embodiments of —OC$_{1-6}$substituted-alkyleneNR$_7$R$_8$ include, for example, —O—CH$_2$CH$_2$CH(oxetanyl)-N(CH$_3$)$_2$ or —O—CH$_2$CH$_2$CH$_2$—NH(CH$_3$). It is particularly preferred that R$_6$ is —OC$_{1-6}$substituted-alkyleneNR$_7$R$_8$ when R$_3$, R$_4$, and R$_5$ are each F.

R$_7$ and R$_8$ can be the same or different. R$_7$ and R$_8$ can each be independently H, C$_{1-6}$alkyl, substituted C$_{1-6}$alkyl, —C(O)C$_{1-6}$alkyl, or aryl; or R$_7$ and R$_8$ together form a heterocyclic ring. Preferably, R$_7$ and R$_8$ are independently H or C$_{1-6}$alkyl. In other embodiments R$_7$ is H and R$_8$ is C$_{1-6}$alkyl. In other embodiments R$_7$ is H and R$_8$ is substituted C$_{1-6}$alkyl. Preferred substituents include trihaloalkyl such as trifluoromethyl. In other embodiments R$_7$ is H and R$_8$ is —C(O)C$_{1-6}$alkyl, wherein preferred alkyl groups are methyl, ethyl, propyl, isopropyl, sec-butyl, and tert-butyl. In yet other embodiments, R$_7$ is H and R$_8$ is aryl, for example phenyl or naphthyl. Alternatively R$_7$ and R$_8$ together form a heterocyclic ring such as morpholinyl, piperidinyl, and piperazinyl. Preferably, R$_7$ and R$_8$ are independently H or methyl.

In certain embodiments wherein R$_6$ is —OC$_{3-6}$cycloalkyleneNR$_7$R$_8$, the C$_{3-6}$cycloalkylene is cyclopropylene or cyclobutylene, preferably, cyclobutylene. It is particularly preferred that R$_6$ is —OC$_{3-6}$cycloalkyleneNR$_7$R$_8$ when R$_3$, R$_4$, and R$_5$ are each F.

Preferred compounds of formula II include, for example, those compounds set forth in Table 2 below:

TABLE 2

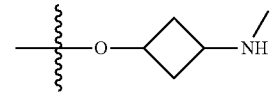 [SMILES: *OC1CC(NC)C1]

| R$_1$ | R$_2$ | R$_3$ | R$_4$ | R$_5$ | R$_6$ |
|---|---|---|---|---|---|
| Cl | H | H | F | F | F |
| Cl | —CH(CH$_3$)CF$_3$ (S) | H | F | F | F |
| Cl | —CH(CH$_3$)CF$_3$ (R) | H | F | F | F |
| Cl | —CH(CH$_3$)CF$_3$ (S,R) | H | F | F | F |
| Cl | —CH(CH$_3$)CF$_3$ (S) | H | F | F | —OCH$_2$CH$_2$CH$_2$NHCH$_3$ |
| Cl | —CH(CH$_3$)CF$_3$ (R) | H | F | F | —OCH$_2$CH$_2$CH$_2$NHCH$_3$ |
| Cl | —CH(CH$_3$)CF$_3$ (S,R) | H | F | F | —OCH$_2$CH$_2$CH$_2$NHCH$_3$ |
| Cl | H | H | F | F | —OCH$_2$CH$_2$CH$_2$NHCH$_3$ |
| Cl | —CH(CH$_3$)CF$_3$ (S) | H | F | F | —OCH$_2$CH$_2$CH$_2$N(CH$_3$)$_2$ |
| Cl | —CH(CH$_3$)CF$_3$ (R) | H | F | F | —OCH$_2$CH$_2$CH$_2$N(CH$_3$)$_2$ |
| Cl | —CH(CH$_3$)CF$_3$ (S,R) | H | F | F | —OCH$_2$CH$_2$CH$_2$N(CH$_3$)$_2$ |
| Cl | —CH(CH$_3$)CF$_3$ (S) | H | F | F | 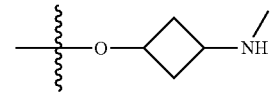 |
| Cl | —CH(CH$_3$)CF$_3$ (R) | H | F | F | 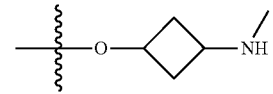 [SMILES: *OC1CC(NC)C1] |
| Cl | —CH(CH$_3$)CF$_3$ (S,R) | H | F | F | 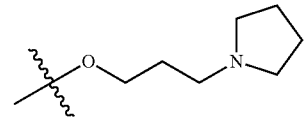 [SMILES: *OCCCN1CCCC1] |
| Cl | —CH(CH$_3$)CF$_3$ (S) | H | F | F | 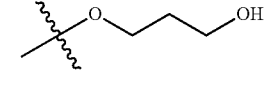 [SMILES: *OCCCO] |
| Cl | —CH(CH$_3$)CF$_3$ (S) | H | F | F | 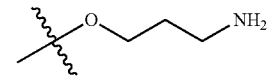 [SMILES: *OCCCN] |
| Cl | —CH(CH$_3$)CF$_3$ (S) | H | F | F |  |

TABLE 2-continued
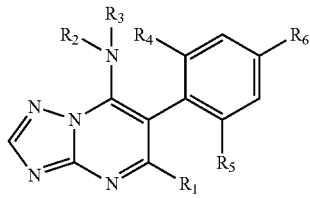
| R₁ | R₂ | R₃ | R₄ | R₅ | R₆ |
|----|----|----|----|----|----|
| Cl | —CH(CH₃)CF₃ (S) | H | F | F | 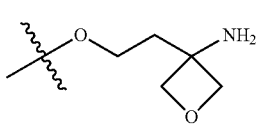 [SMILES: *OCCC1(N)COC1] |
| Cl | —CH(CH₃)CF₃ (S) | H | F | F | 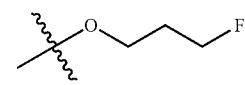 [SMILES: *OCCCF] |
| Cl | —CH(CH₃)CF₃ (S) | H | F | F | 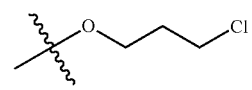 [SMILES: *OCCCCl] |
| Cl | —CH(CH₃)CF₃ (S) | H | F | F | 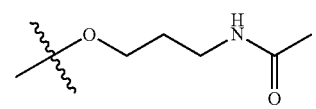 [SMILES: *OCCCNC(C)=O] |
| Cl | —CH(CH₃)CF₃ (S) | H | F | F | 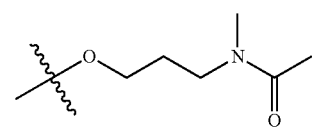 [SMILES: *OCCCN(C)C(C)=O] |
| Cl | —CH(CH₃)CF₃ (S) | H | F | F | 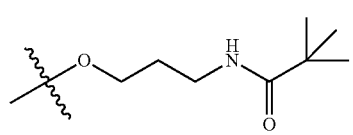 [SMILES: *OCCCNC(=O)C(C)(C)C] |
| Cl | —CH(CH₃)CF₃ (S) | H | F | F | 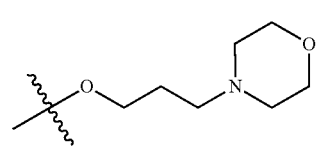 [SMILES: *OCCCN1CCOCC1] |
| Cl | —CH(CH₃)CF₃ (S) | H | F | F | 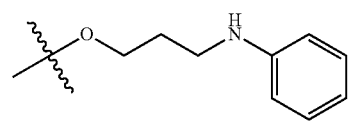 [SMILES: *OCCCNc1ccccc1] |
| Cl | —CH(CH₃)CF₃ (S) | H | F | F | 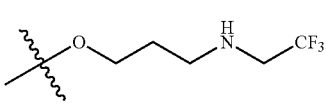 [SMILES: *OCCCNCC(F)(F)F] |

Pyridopyridazine and pyridotriazine compounds for use in the invention include those of formula III:

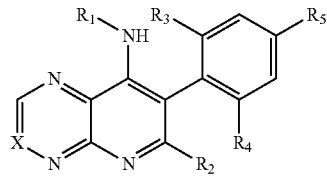

wherein

X is CH or N;

$R_1$ is $C_{1-6}$alkyl or substituted $C_{1-6}$alkyl;

$R_2$ is F, Cl, or Br;

$R_3$ is F, Cl, or Br;

$R_4$ is F, Cl, or Br; and $R_5$ is F, Cl, or Br.

Stereoisomeric forms of the compounds of formula III, for example, enantiomers, diastereomers, and atropisomers, are also within the scope of the invention, as are pharmaceutically acceptable salts of any compound or stereoisomer of formula III.

Preferred embodiments of compounds of formula III are those wherein X is CH. Other embodiments include those compounds of formula III wherein X is N.

Preferably, $R_1$ is $C_{1-6}$alkyl, for example, methyl, ethyl, propyl, isopropyl, butyl, sec-butyl, and tert-butyl. In other embodiments, $R_1$ is substituted $C_{1-6}$alkyl. Exemplary substituents include, for example, halogen or trihalo alkyl such as —$CF_3$. Preferred substituted $C_{1-6}$alkyl include —CH($CH_3$)$CF_3$, and all stereoisomers thereof, and —$CH_2CF_3$.

Particularly preferred compounds of formula III for use in the invention are those wherein $R_2$ is Cl or F, preferably Cl.

In some embodiments, $R_3$ is F. In other embodiments, $R_3$ is Cl. In yet other embodiments, $R_3$ is Br.

In some embodiments, $R_4$ is F. In other embodiments, $R_4$ is Cl. In yet other embodiments, $R_4$ is Br.

In some embodiments, $R_5$ is F. In other embodiments, $R_5$ is Cl. In yet other embodiments, $R_5$ is Br.

Also preferred are compounds of formula III wherein at least one of $R_3$, $R_4$, and $R_5$ is F. In alternative embodiments, each of $R_3$, $R_4$, and $R_5$ is F.

Preferred compounds of III include

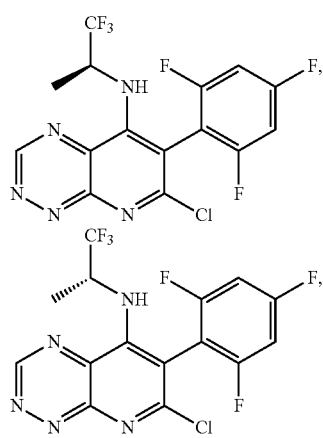

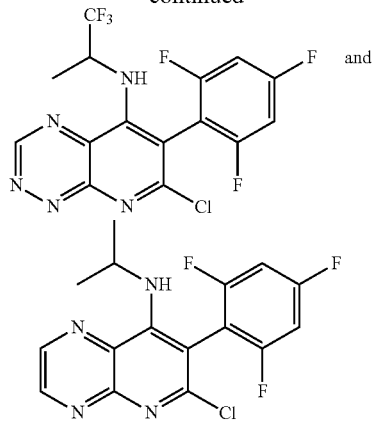

Pyridazine compounds for use in the invention include those of formula IV:

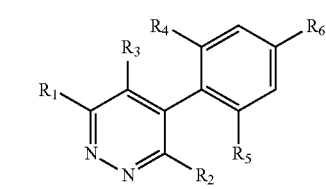

wherein $R_1$ is $C_{1-6}$alkyl;

$R_2$ is F, Cl, or Br;

$R_3$ is phenyl, pyridinyl, pyrimidyl, pyrazinyl, imidazolyl, pyrrolyl, pyrazolyl, quinolunyl, isoquinolinyl, thienyl, or furyl, each of which may be optionally substituted with one or more of F, Cl, or Br;

$R_4$ is F, Cl, or Br;

$R_5$ is F, Cl, or Br; and $R_6$ is F, Cl, or Br.

Stereoisomeric forms of the compounds of formula IV, for example, enantiomers, diastereomers, and atropisomers, are also within the scope of the invention, as are pharmaceutically acceptable salts of any compound or stereoisomer of formula IV.

Particularly preferred compounds of formula IV for use in the invention are those wherein $R_1$ is methyl, ethyl, propyl, isopropyl, butyl, sec-butyl, and tert-butyl, preferably methyl. Also preferred are those compounds wherein $R_2$ is Cl. Other preferred compounds of formula IV are those wherein $R_2$ is F. In other preferred compounds of formula IV, $R_2$ is Br.

Preferred embodiments of the invention include those compounds of formula IV wherein $R_3$ is phenyl. Particularly preferred are embodiments wherein $R_3$ is phenyl substituted with halo such as Cl. In other embodiments, $R_3$ is thienyl, preferably thienyl substituted with halo such as chloro.

In some embodiments, $R_4$ is F. In other embodiments, $R_4$ is Cl. In yet other embodiments, $R_4$ is Br.

In some embodiments, $R_5$ is F. In other embodiments, $R_5$ is Cl. In yet other embodiments, $R_5$ is Br.

In some embodiments, $R_6$ is F. In other embodiments, $R_6$ is Cl. In yet other embodiments, $R_6$ is Br.

Other preferred compounds of formula IV include those wherein at least one of $R_4$, $R_5$, and $R_6$ is F. In yet other embodiments, each of $R_4$, $R_5$, and $R_6$ is F.

Preferred compounds of formula IV are

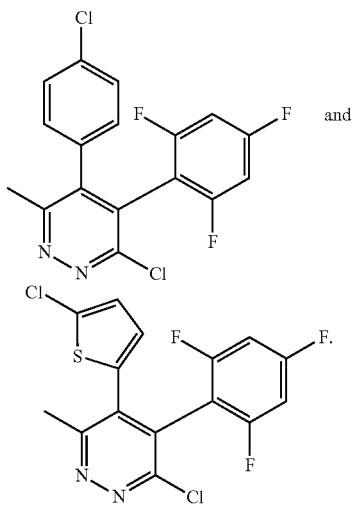

and

As used herein, "$C_{1-6}$alkyl" refers to straight or branched aliphatic groups having from 1 to 6 carbon atoms. Examples include methyl, ethyl, propyl, isopropyl, butyl, isobutyl, tert-butyl, pentyl, isopentyl, hexyl, and the like. "$C_{1-6}$alkylene" refers to straight or branched aliphatic groups having from 1 to 6 carbon atoms and having two points of attachment, for example, methylene (—CH$_2$—), ethylene (—CH$_2$—CH$_2$—), propylene (—CH$_2$—CH$_2$—CH$_2$—), and the like.

As used herein, "substituted $C_{1-6}$alkyl" refers to $C_{1-6}$alkyl groups as defined herein, substituted with another moiety that is, for example, F, Cl, Br, CF$_3$, or heterocycloalkyl.

As used herein "$C_{3-6}$cycloalkyl" refers to a cyclic aliphatic group having from 3 to 6 carbon atoms. Examples include cyclopropyl, cyclobutyl, cyclopentyl, and cyclohexyl. "$C_{3-6}$cycloalkylene" refers to a cyclic aliphatic group having from 3 to 6 carbon atoms and having two points of attachment, for example, cyclopropylene, cyclobutylene, cyclopentylene, and cyclohexylene.

As used herein, "halo" or "halogen" refers to F, Cl, Br, or I.

As used herein "heterocyclo$C_{3-6}$alkyl" or "heterocycloalkyl" refers to an aliphatic cyclic moiety that includes from 3-6 carbon atoms, in addition to 1, 2 or 3 heteroatoms that are N, O, or S.

As used herein, "stereoisomers" refers to all enantiomerically/diastereomerically pure and enantiomerically/diastereomerically enriched compounds of the invention. Atropisomers, that is, stereoisomers resulting from hindered rotation about single bonds, are also within the scope of the term, "stereoisomers."

As used herein, "pharmaceutically acceptable salt" refers to a salt of a compound of the invention that is generally considered safe for pharmaceutical use. Examples include, for example, hydrochloric acid, sulfuric, fumaric, succinic, ascorbic, maleic, methanesulfonic, and isoethonic acid salts.

Compounds for use within the scope of the invention can be prepared according to methods known in the art. For example, certain phenylpyrimidine compounds within the scope of formula I can be prepared according to the sequence set forth in Scheme 1. Those skilled in the art can readily access the enantiomers using a comparable sequence of reactions.

Scheme 1

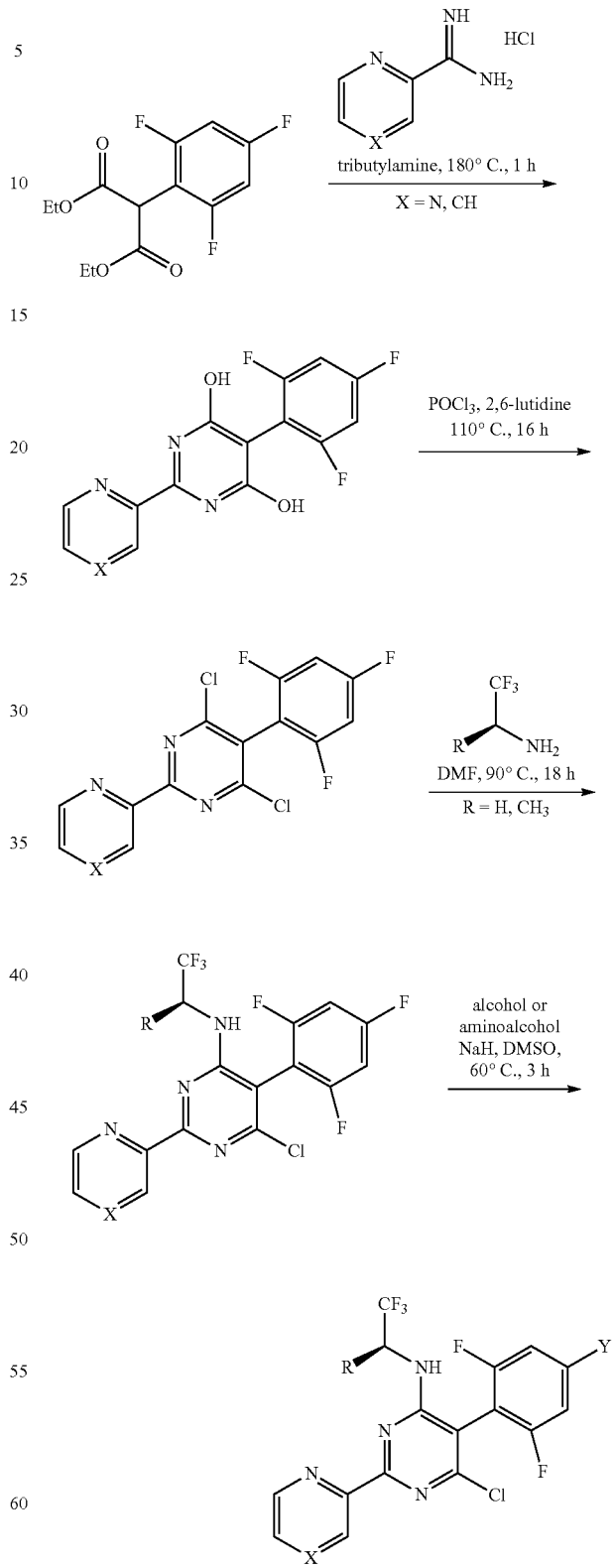

Phenylpyrimidine compounds within the scope of formula I that can be made according to the procedures set forth in Scheme 1 include, for example, those of Table 3.

TABLE 3

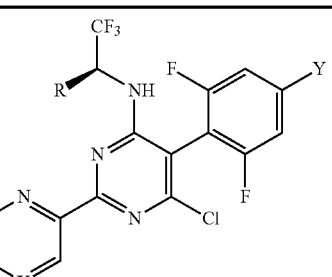

| CNDR# | X | R | Y |
|---|---|---|---|
| 51549 | N | CH₃ (S) | F |
|  | N | CH₃ (R) | F |
|  | N | CH₃ (S,R) | F |
| 51550 | N | H | F |
| 51552 | CH | CH₃ (S) | F |
|  | CH | CH₃ (R) | F |
|  | CH | CH₃ (S,R) | F |
| 51553 | CH | H | F |
| 51554 | N | CH₃ (S) | -O-CH₂CH₂CH₂-N(CH₃)₂ |
|  | N | CH₃ (R) | -O-CH₂CH₂CH₂-N(CH₃)₂ |
|  | N | CH₃ (S,R) | -O-CH₂CH₂CH₂-N(CH₃)₂ |
| 51557 | CH | H | -O-CH₂CH₂CH₂-N(CH₃)₂ |
| 51560 | CH | H | OtBu |
| 51561 | CH | CH₃ (S) | -O-CH₂CH₂CH₂-N(CH₃)₂ |
| 51562 | CH | CH₃ (S) | -CH₂CH₂CH₂-NH-CH₃ |

Certain triazolopyrimidine compounds within the scope of formula II can be prepared according to the sequence set forth in Scheme 2. Those skilled in the art can readily access the enantiomers using a comparable sequence of reactions.

Scheme 2

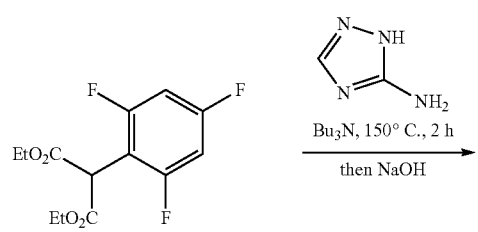

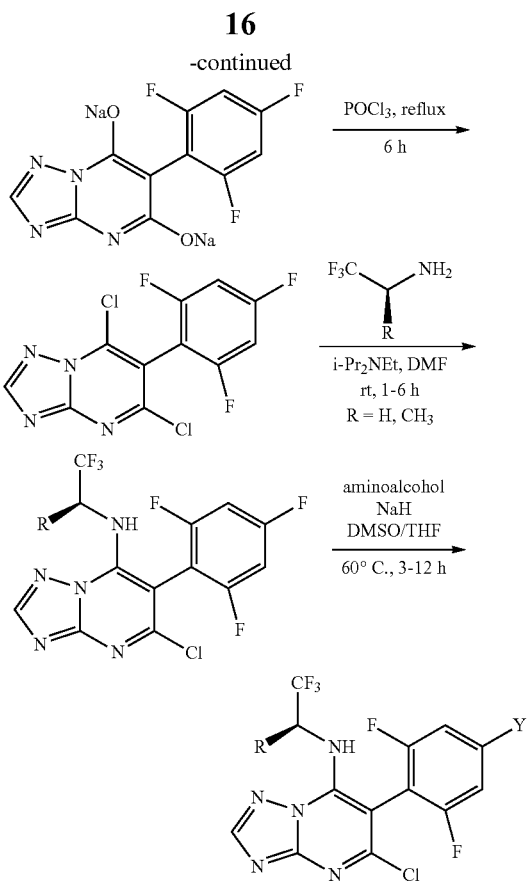

Triazolopyrimidine compounds of formula II that can be prepared according to the procedures set forth in Scheme 2 include, for example, those set forth in Table 4.

TABLE 4

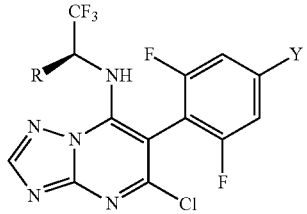

| CNDR# | R | Y |
|---|---|---|
| 51539 (7) | H | F |
| 51551 | CH₃ (S) | F |
|  | CH₃ (R) | F |
|  | CH₃ (S,R) | F |
| 51533 Cevipabulin (8) | CH₃ (S) | -O-CH₂CH₂CH₂-NH-CH₃ |
|  | CH₃ (R) | -O-CH₂CH₂CH₂-NH-CH₃ |
|  | CH₃ (S,R) | -O-CH₂CH₂CH₂-NH-CH₃ |

TABLE 4-continued

| CNDR# | R | Y |
|---|---|---|
| 51534 (9) | H | —O—CH2CH2CH2—NHCH3 |
| 51555 | CH3 (S) | —O—CH2CH2CH2—N(CH3)2 |
|  | CH3 (R) | —O—CH2CH2CH2—N(CH3)2 |
|  | CH3 (S,R) | —O—CH2CH2CH2—N(CH3)2 |
| 51556 | CH3 (S) | —O-cyclobutyl-NHCH3 |
|  | CH3 (R) | —O-cyclobutyl-NHCH3 |
|  | CH3 (S,R) | —O-cyclobutyl-NHCH3 |
| 51569 | CH3 (S) | —O—CH2CH2CH2—N(pyrrolidine) |
| 51567 | CH3 (S) | —O—CH2CH2CH2—OH |
| 51570 | CH3 (S) | —O—CH2CH2CH2—NH2 |
| 51572 | CH3 (S) | —O—CH2CH2—(3-aminooxetane) |
| 51588 | CH3 (S) | —O—CH2CH2CH2—F |
| 51591 | CH3 (S) | —O—CH2CH2CH2—Cl |
| 51589 | CH3 (S) | —O—CH2CH2CH2—NHC(O)CH3 |
| 51593 | CH3 (S) | —O—CH2CH2CH2—N(CH3)C(O)CH3 |
| 51595 | CH3 (S) | —O—CH2CH2CH2—NHC(O)C(CH3)3 |
| 51596 | CH3 (S) | —O—CH2CH2CH2—N(morpholine) |
| 51598 | CH3 (S) | —O—CH2CH2CH2—NH-phenyl |
| 51599 | CH3 (S) | —O—CH2CH2CH2—NH—CH2CF3 |

Compounds of formula III can be prepared, for example, according to the sequence depicted in Scheme 3.

Scheme 3

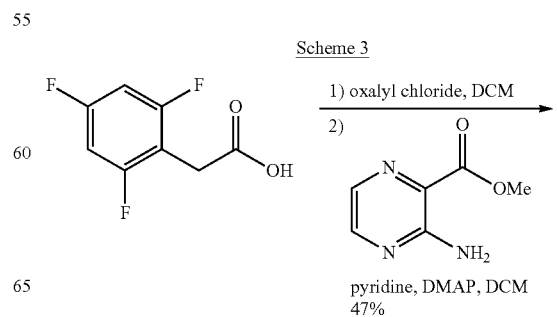

1) oxalyl chloride, DCM
2) methyl 3-aminopyrazine-2-carboxylate, pyridine, DMAP, DCM
47%

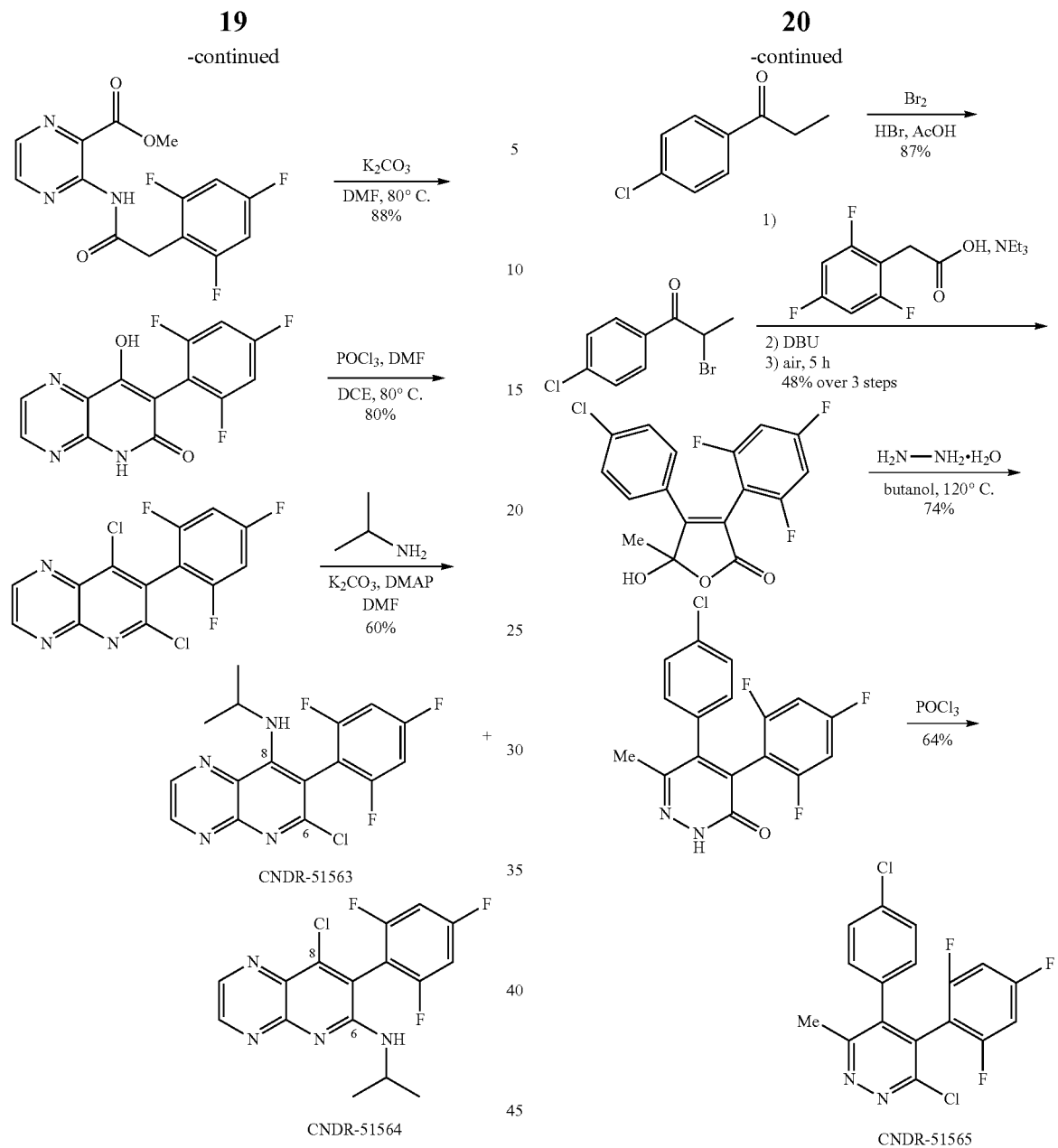
Certain preferred compounds of formula IV can be prepared according to the sequences depicted in Schemes 4A and 4B.
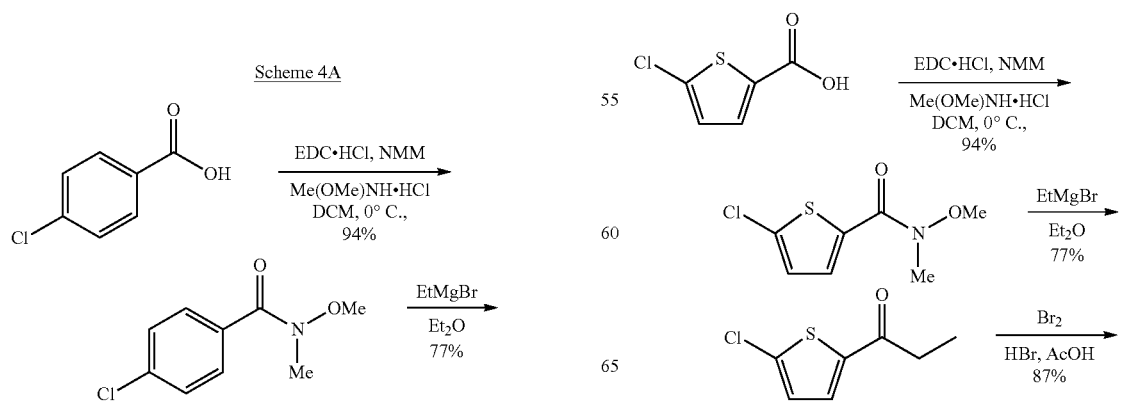

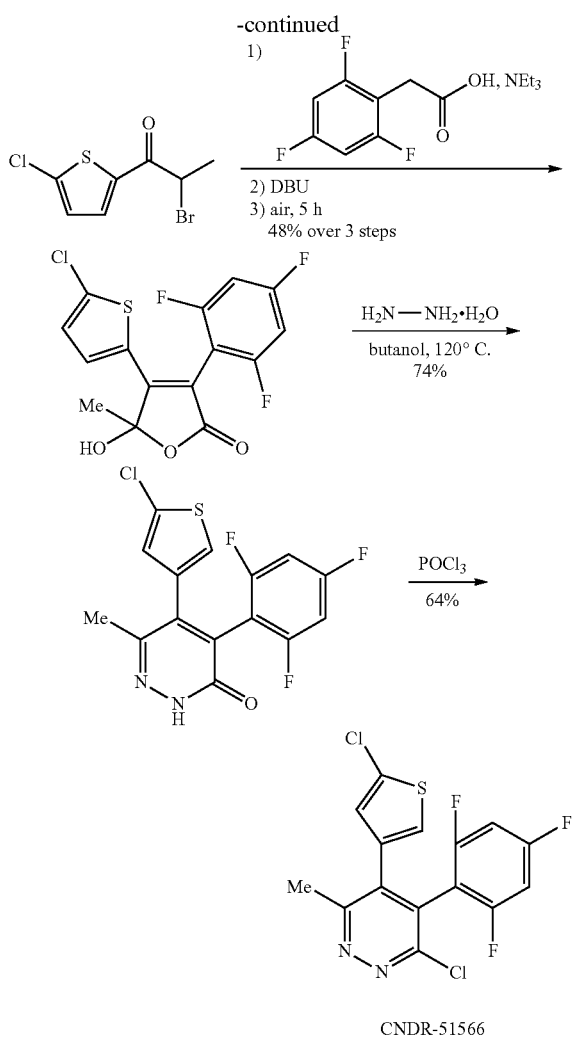

CNDR-51566

The MT-stabilizing properties of triazolopyrimidines was investigated in a cell-free MT-polymerization assay, as well in a cell-based assay (HEK/QBI 293 cells) that measures changes in acetyl-tubulin (AcTub), a biomarker of stable MTs. (Laferriere, N.; MacRae, T.; Brown, D. Tubulin synthesis and assembly in differentiating neurons. Biochemistry and Cell Biology 1997, 75, 103-117; Black, M.; Baas, P.; Humphries, S. Dynamics of alpha-tubulin deacetylation in intact neurons. J Neurosci 1989, 9, 358). The results from the cell-free studies (data not shown) are in complete agreement with a published report (Beyer, C. F.; Zhang, N.; Hernandez, R.; Vitale, D.; Lucas, J.; Nguyen, T.; Discafani, C.; Ayral-Kaloustian, S.; Gibbons, J. J. TTI-237: a novel microtubule-active compound with in vivo antitumor activity. Cancer Res 2008, 68, 2292-300) and confirmed that the triazolopyri-midines exhibit MT-stabilizing activity similar to that of paclitaxel. The results of the cell-based studies, summarized in FIG. 1, revealed that triazolopyrimidines 7, 8, and 9 (see Table 4) produce a dose-dependent elevation in AcTub. Furthermore, these compounds caused significant increases of detyrosinated α-tubulin (GluTub), another marker of stable MTs (data not shown). Notably, both 8 and 9 were found to be significantly more effective than epoD at 100 nM (FIG. 1).

To confirm these results and to ensure that triazolopyrimidine treatment results in an increased organization of the MT-network, rather than disorganized tubulin aggregates, MT structure in HEK/QBI293 cells as determined by AcTub immunofluo-rescence was examined after 4 h of incubation with cevipabulin. Cells that were treated with 100 nM cevipabulin (8) revealed a large increase in highly organized, AcTub-positive MTs relative to control cells, with the intensity of staining exceeding that observed with 100 nM of the known MT-stabilizing agent, epothilone D (epoD). In contrast, the MT-destabilizing agent, colchicine, led to a significant loss of AcTub staining (data not shown).

TABLE 5

Activity of some triazolopyrimidine embodiments of the invention in a cell-based assay in which MT stabilization was determined by measuring the relative increase of acetyl-tubulin (AcTub) levels after compound treatment.

| Structure | Compound # | Fold-Increase in AcTub (dose of maximal effect) |
| --- | --- | --- |
| 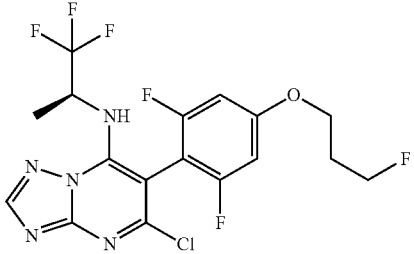 [SMILES: C[C@H](Nc1c(-c2c(F)cc(OCCCF)cc2F)c(Cl)nc2ncnn12)C(F)(F)F] | 51588 | 3.2 (10 μM) |

TABLE 5-continued

Activity of some triazolopyrimidine embodiments of the invention in a cell-based assay in which MT stabilization was determined by measuring the relative increase of acetyl-tubulin (AcTub) levels after compound treatment.

| Structure | Compound # | Fold-Increase in AcTub (dose of maximal effect) |
|---|---|---|
| 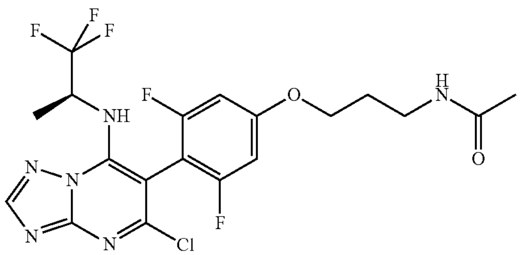 [SMILES: CC(=O)NCCCOc1cc(F)c(-c2c(Cl)nc3ncnn3c2N[C@@H](C)C(F)(F)F)c(F)c1] | 51589 | 10.2 (1 µM) |
| 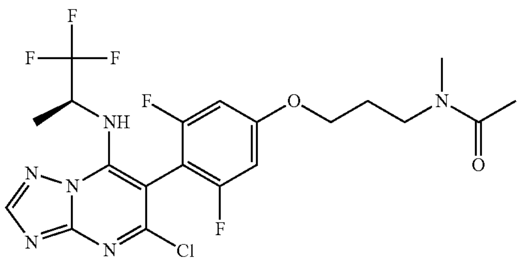 [SMILES: CC(=O)N(C)CCCOc1cc(F)c(-c2c(Cl)nc3ncnn3c2N[C@@H](C)C(F)(F)F)c(F)c1] | 51593 | 1.9 (10 µM) |
| 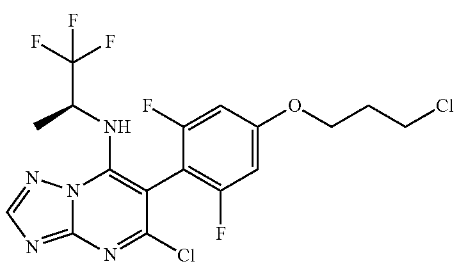 [SMILES: C[C@H](Nc1c(-c2c(F)cc(OCCCCl)cc2F)c(Cl)nc2ncnn12)C(F)(F)F] | 51591 | 3.7 (10 µM) |
| 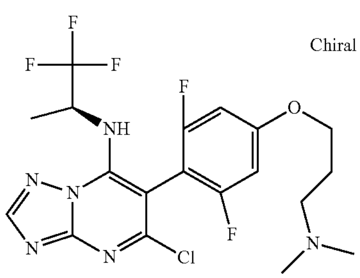 [SMILES: C[C@H](Nc1c(-c2c(F)cc(OCCCN(C)C)cc2F)c(Cl)nc2ncnn12)C(F)(F)F] | 51555 | 21.5 (1 µM) |
| 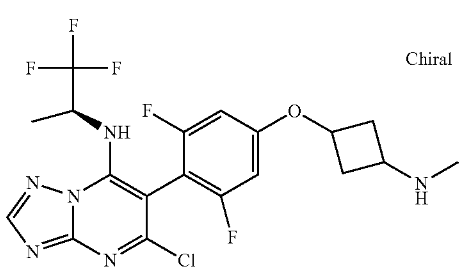 [SMILES: CNC1CC(Oc2cc(F)c(-c3c(Cl)nc4ncnn4c3N[C@@H](C)C(F)(F)F)c(F)c2)C1] | 51556 | 10.2 (1 µM) |

TABLE 5-continued

Activity of some triazolopyrimidine embodiments of the invention in a cell-based assay in which MT stabilization was determined by measuring the relative increase of acetyl-tubulin (AcTub) levels after compound treatment.

| Structure | Compound # | Fold-Increase in AcTub (dose of maximal effect) |
|---|---|---|
| 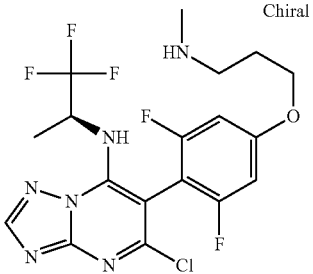 [SMILES: CNCCCOc1cc(F)c(-c2c(Cl)nc3ncnn3c2N[C@@H](C)C(F)(F)F)c(F)c1] Chiral | 51533 | 4.7 (0.1 μM) |
| 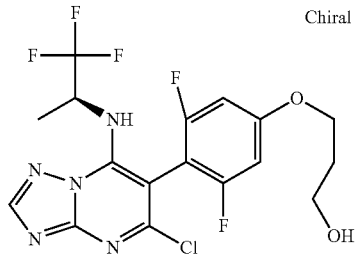 [SMILES: C[C@H](Nc1c(-c2c(F)cc(OCCCO)cc2F)c(Cl)nc2ncnn12)C(F)(F)F] Chiral | 51567 | 10.1 (1 μM) |
| 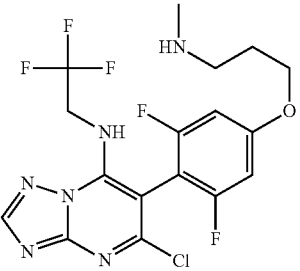 [SMILES: CNCCCOc1cc(F)c(-c2c(Cl)nc3ncnn3c2NCC(F)(F)F)c(F)c1] | 51534 | 7.2 (1 μM) |

TABLE 6

Activity of some phenylpyrimidine and pyridazine embodiments of the invention in a cell-based assay in which MT stabilization was determined by measuring the relative increase of acetyl-tubulin (AcTub) levels after compound treatment.

| Structure | Compound # | Fold-Increase in AcTub (dose of maximal effect) |
|---|---|---|
| 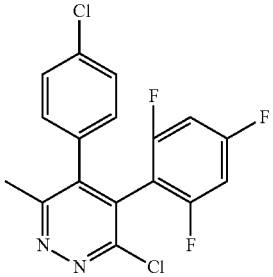 [SMILES: Cc1nnc(Cl)c(-c2c(F)cc(F)cc2F)c1-c1ccc(Cl)cc1] | 51565 | 4.6 (10 μM) |

TABLE 6-continued

Activity of some phenylpyrimidine and pyridazine embodiments of the invention in a cell-based assay in which MT stabilization was determined by measuring the relative increase of acetyl-tubulin (AcTub) levels after compound treatment.

| Structure | Compound # | Fold-Increase in AcTub (dose of maximal effect) |
|---|---|---|
| 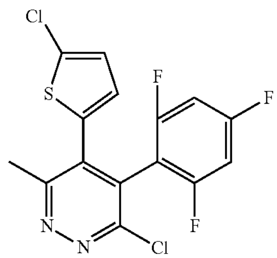 [SMILES: Cc1nnc(Cl)c(-c2c(F)cc(F)cc2F)c1-c1ccc(Cl)s1] | 51566 | 2.5 (10 μM) |
| Chiral | 51554 | 4.9 (0.1 μM) |
| 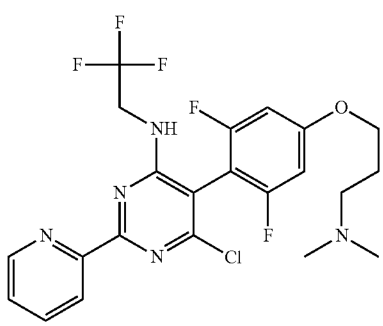 [SMILES: CN(C)CCCOc1cc(F)c(-c2c(Cl)nc(-c3ccccn3)nc2NCC(F)(F)F)c(F)c1] | 51557 | 3.2 (0.1 μM) |
| Chiral | 51561 | 6.1 (0.1 μM) |

TABLE 6-continued

Activity of some phenylpyrimidine and pyridazine embodiments of the invention in a cell-based assay in which MT stabilization was determined by measuring the relative increase of acetyl-tubulin (AcTub) levels after compound treatment.

| Structure | Compound # | Fold-Increase in AcTub (dose of maximal effect) |
|---|---|---|
| [Chiral structure] | 51562 | 6.2 (0.1 μM) |
| [Chiral structure] | 51549 | 3.0 (1 μM) |
| [Chiral structure] | 51552 | 3.7 (1 μM) |

TABLE 7

Brain and plasma levels of some triazolopyrimidine and phenylpyrimidine embodiments of the invention 1 hour after a 5 mg/kg intraperitoneal injection of compound.

| Compound | Brain nM (SD) | Plasma nM (SD) | Brain/Plasma |
|---|---|---|---|
| 51549 | 2870 (112) | 4946 (151) | 0.58 |
| 51552 | 1479 (112) | 4323 (862) | 0.34 |
| 51555 | 1349 (208) | 4934 (545) | 0.27 |
| 51561 | 701 (41) | 2120 (160) | 0.33 |

The MT-stabilizing properties of additional triazolopyrimidines, phenylpyrimidines, and pyridazines was investigated in a cell-free MT-polymerization assay, as well in the aforementioned cell-based assay (HEK/QBI 293 cells) that measures changes in acetyl-tubulin (AcTub), a biomarker of stable MTs (Laferriere, N.; MacRae, T.; Brown, D. Tubulin synthesis and assembly in differentiating neurons. Biochemistry and Cell Biology 1997, 75, 103-117; Black, M.; Baas, P.; Humphries, S. Dynamics of alpha-tubulin deacetylation in intact neurons. J Neurosci 1989, 9, 358). The testing of triazolopyrimidines (Table 5) and phenylpyrimidines (Table 6) in the cell-based studies revealed that a number of examples from each series produce an increase of AcTub relative to vehicle-treated cells, with the magnitude of the increase and the concentration of maximal effect varying among the various examples.

Figure 13A:
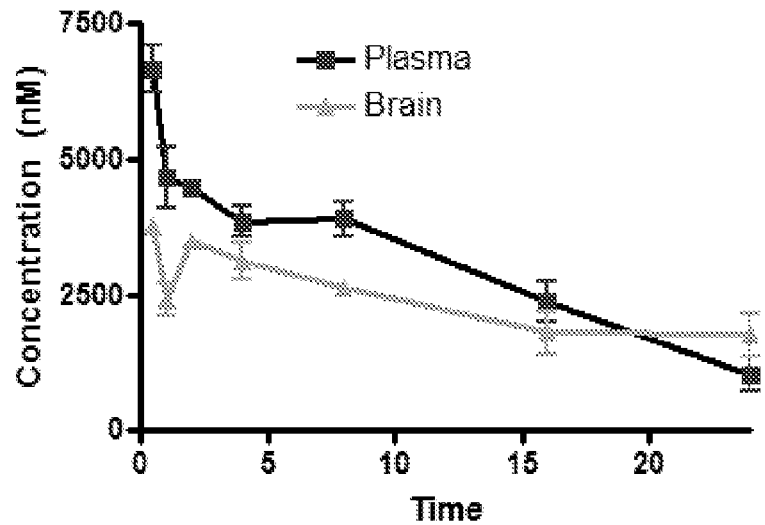
FIGS. 13A and 13B depicts pharmacokinetic testing of CNDR-51549 (13A) and CNDR-51555 (13B), demonstrating that both compounds have brain exposure.
Figure 13:
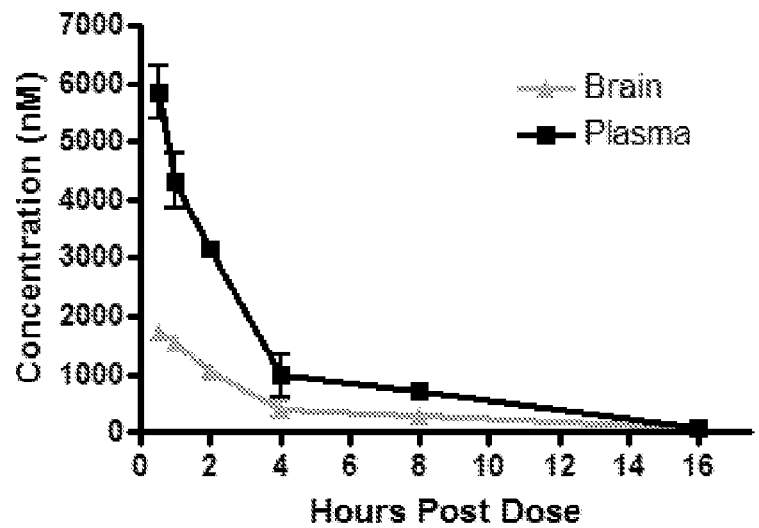
Figure 14:
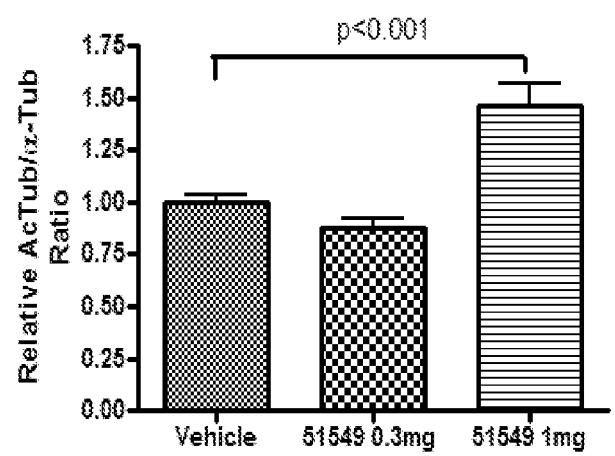
FIG. 14 depicts CNDR-51549 administration at 1 mg/kg daily to wild-type mice. This administration results in an increase in the fraction of brain α-tubulin that is acetylated (AcTub).

For utility in neurodegenerative diseases, MT-stabilizing compounds must cross the blood-brain barrier (BBB) and enter the brain. As summarized in Table 7, a number of examples show concentrations in the brain that exceed 0.5 μM an hour after administration of a 5 mg/kg dose, with brain-to-plasma concentration ratios of ~0.3 or higher. The relative brain exposures predicted by the one hour analysis of brain and plasma compound levels were confirmed by more complete pharmacokinetic analyses, as exemplified by the profiles of CNDR-51549 and CNDR-51555 shown in FIG. 13. Thus, unlike many previously described MT-stabilizing agents, including cevepabulin, which do not cross the BBB, multiple phenylpyrimidine and triazolopyrimidine examples were unexpectedly found to be brain-penetrant. Moreover, CNDR-51549 was found to cause an increase of AcTub levels in the brains of wild-type mice 3 days after receiving a once-daily 1 mg/kg dose, as shown in FIG. 14. This is reminiscent of what has been demonstrated for other brain-penetrant MT-stabilizing agents (see Brunden K R, Yao Y, Potuzak J S, Ibarz Ferrer N, Ballatore C, James M J, Hogan A L, Trojanowski J Q, Amos Smith A B, III and Lee VM-Y. The Characterization of Microtubule-Stabilizing Drugs as Possible Therapeutic Agents for Alzheimer's Disease and Related Tauopathies. Pharmacol. Res., 2011, 63:341-351), indicating that this and other examples described herein are appropriate for the treatment of neurodegenerative disease.

The compounds of formula I can be administered by a variety of methods known to one skilled in the art. Methods of administration include, but are not limited to, intradermal, intramuscular, intraperitoneal, intravenous, subcutaneous, intranasal, epidural, and oral routes. The compounds may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the compounds into the central nervous system by any suitable route, including intraventricular and intrathecal injection.

The practice of the invention can be further understood by reference to the following examples, which are provided by way of illustration and are not intended to be limiting of the invention.

Materials and Methods.

All solvents were reagent grade. All reagents were purchased from Aldrich or Acros and used as received. Thin layer chromatography (TLC) was performed with 0.25 mm E Merck pre-coated silica gel plates. Flash chromatography was performed with silica gel 60 (particle size 0.040-0.062 mm) supplied by Silicycle and Sorbent Technologies. Spots were detected by viewing under a UV light. Yields refer to chromatographically and spectroscopically pure compounds. Infrared spectra were recorded on a Jasco Model FT/IR-480 Plus spectrometer. Proton ($^1$H) and carbon ($^{13}$C) NMR spectra were recorded on a Bruker AMX-500 spectrometer. Chemical shifts were reported relative to solvents. High-resolution mass spectra were measured at the University of Pennsylvania Mass Spectrometry Service on a Waters LCT Premier XE LC/MS system. Analytical reversed-phased (Sunfire™ C18; 4.6×50 mm, 5 mL) high-performance liquid chromatography (HPLC) was performed with a Water binary gradient module 2525 equipped with Waters 2996 PDA and Water micromass ZQ. All samples were analyzed employing a linear gradient from 10% to 90% of acetonitrile in water over 8 minutes and flow rate of 1 mL/min. Preparative reverse phase HPLC purification was performed on a Gilson HPLC system equipped with Gilson 333 pumps, a 215 Liquid Handler, 845Z injection module, and UV detector, employing Waters SunFire™ prep C18 OBD™ columns (5 μm 19×50 or 19×100 mm) All samples were purified employing a linear gradient from 10% to 90% of acetonitrile in water over 15 minutes and flow rate of 20 mL/min. Unless otherwise stated, all final compounds were found to be >95% as determined by HPLC/MS and NMR.

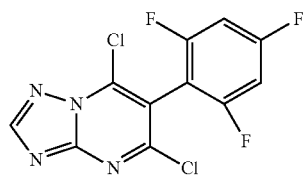 [SMILES: Fc1cc(F)c(-c2c(Cl)nc3ncnn3c2Cl)c(F)c1]

5,7-Dichloro-6-(2,4,6-trifluorophenyl)-[1,2,4]triazolo[1,5-a]pyrimidine

Following a reported procedure, (Zhang et al., J. Med. Chem., 2007, 50, 319-327) a slurry of 2-(2,4,6-trifluorophenyl)malonate (1.19 g, 4.10 mmol) and aminotriazole (362 mg, 4.31 mmol) in tributylamine (1.03 μL) was heated to 170° C. for 2 h. The resulting homogeneous brown mixture was cooled to 130° C. and toluene (4 mL) was added before cooling to 50° C. A solution of NaOH (360 μL, 50% aqueous) was added and the precipitated solids were collected by vacuum filtration, washed with cold toluene, and dried to afford the bis-sodium salt of 6-(2,4,6-trifluorophenyl)-[1,2,4]triazolo[1,5-c]pyrimidine-5,7-diol as a beige powder (1.24 g, 3.80 mmol, 93% yield).

A mixture of bis-sodium 6-(2,4,6-trifluorophenyl)-[1,2,4]triazolo[1,5-a]pyrimidine-5,7-diolate (300 mg, 0.9 mmol) and phosphorus oxychloride (1.5 mL, 16 mmol) was heated to 130° C. for 6 h. The reaction mixture was cooled to room temperature and was carefully quenched with H$_2$O (2 mL). This aqueous mixture was extracted with EtOAc (3×5 mL) and the combined organic layers were dried (MgSO$_4$), filtered, and concentrated to an orange oil that was used without further purification (143 mg, 0.448 mmol, 50% yield): $^1$H NMR (500 MHz, CDCl$_3$) δ 8.62 (s, 1H), 6.94-6.89 (m, 2 H); MS (ESI$^+$) 319.00 [M+H$^+$].

General Procedure A:

According to a reported procedure, (Zhang et al., J. Med. Chem., 2007, 50, 319-327) to 5,7-dichloro-6-(2,4,6-trifluorophenyl)-[1,2,4]triazolo[1,5-a]pyrimidine (1.0 equiv) in DMF (0.1 M) at room temperature was added i-Pr$_2$NEt (3.0 equiv) and the appropriate amine (3.0 equiv). The orange solution was stirred for 1-6 h and diluted with H$_2$O. The aqueous phase was extracted with 3×10 mL EtOAc, and the combined organic layers were dried (MgSO$_4$), filtered, and concentrated. The acid-sensitive products were purified by reverse-phase HPLC.

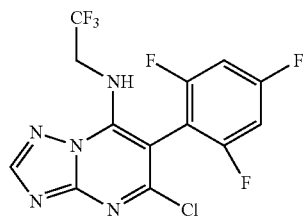 [SMILES: Fc1cc(F)c(-c2c(Cl)nc3ncnn3c2NCC(F)(F)F)c(F)c1]

5-Chloro-N-(2,2,2-trifluoroethyl)-6-(2,4,6-trifluorophenyl)-[1,2,4]triazolo[1,5-a]pyrimidin-7-amine Following General Procedure A using 2,2,2-trifluoroethylamine hydrochloride, reverse-phase HPLC purification afforded the title compound as a colorless solid (14.0 mg, 0.036 mmol, 41% yield): $^1$H NMR (500 MHz, CDCl$_3$) δ 8.41 (s, 1 H), 6.94-6.89 (m, 2 H), 6.20 (bs, 1 H), 4.20 (dq, J=7.7, 8.1 Hz, 2 H). HRMS (ESI) calculated for $C_{13}H_2N_5F_6Cl$ [M+H$^+$] 382.0294, found 382.0299

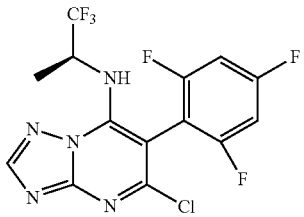 [SMILES: C[C@H](Nc1c(-c2c(F)cc(F)cc2F)c(Cl)nc2ncnn12)C(F)(F)F]

(S)-5-Chloro-6-(2,4,6-trifluorophenyl)-N-(1,1,1-trifluoropropan-2-yl)-[1,2,4]triazolo[1,5-a]pyrimidin-7-amine Following General Procedure A using (2S)-1,1,1-trifluoro-2-propylamine, reverse-phase HPLC purification afforded the title compound as a colorless solid (42.0 mg, 0.106 mmol, 25% yield): $^1$H NMR (500 MHz, CDCl$_3$) δ 8.41 (s, 1 H), 6.95-6.89 (m, 2H), 5.88 (d, J=9.2 Hz, 1 H), 4.69 (bm, 1 H), 1.43 (d, J=6.8 Hz, 3H) ppm; MS (ESI) 396.04 [M+H$^+$].

General Procedure B:

According to a reported procedure, (Zhang et al., J. Med. Chem., 2007, 50, 319-327; Zhang et al., Bioorg. Med. Chem., 2009, 111-118) to a suspension of NaH (4.0 equiv) in a 2:1 mixture of DMSO and THF (0.35 M) was added the aminoalcohol (4.0 equiv), and the mixture was heated to 60° C. for 1 h. The resulting yellow turbid solution was treated with a solution of trifluoroarene (1.0 equiv) in a 1:1 mixture DMSO and THF (0.5 M). The reaction mixture was stirred at 60° C. for 3 h and monitored by LCMS. If the starting material remained after 3 h, additional NaH (4.0 equiv) and aminoalcohol (4.0 equiv) were added, sequentially, and the reaction mixture was heated for 12 h. Following complete consumption of the starting material, the reaction mixture was cooled to room temperature and diluted with H$_2$O and EtOAc. The organic layer was washed with H$_2$O and brine, and the combined aqueous layers were extracted with EtOAc (×3). The combined organic layers were dried (MgSO$_4$), filtered, and concentrated. The crude products were purified by reverse-phase HPLC.

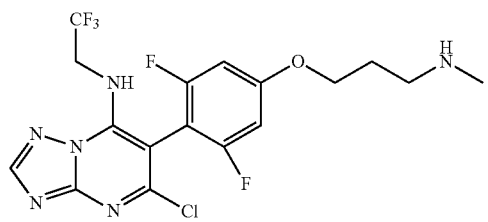 [SMILES: CNCCCOc1cc(F)c(-c2c(Cl)nc3ncnn3c2NCC(F)(F)F)c(F)c1]

5-Chloro-6-(2,6-difluoro-4-(3-(methylamino)propoxy)phenyl)-N-(2,2,2-trifluoroethyl)-[1,2,4]triazolo[1,5-a]pyrimidin-7-amine Following General Procedure B using 3-(methylamino)-1-propanol and 5-chloro-N-(2,2,2-trifluoroethyl)-6-(2,4,6-trifluorophenyl)-[1,2,4]triazolo[1,5-a]pyrimidin-7-amine, reverse-phase HPLC purification afforded the title compound as a colorless solid (6.1 mg, 0.014 mmol, 13% yield): MS (ER$^+$) 450.69 [M+H$^+$].

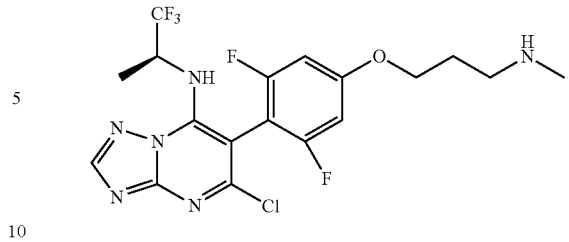

(S)-5-Chloro-6-(2,6-difluoro-4-(3-(methylamino)propoxy)phenyl)-N-(1,1,1-trifluoropropan-2-yl)-[1,2,4]triazolo[1,5-a]pyrimidin-7-amine Following General Procedure B using 3-(methylamino)-1-propanol and (S)-5-chloro-6-(2,4,6-trifluorophenyl)-N-(1,1,1-trifluoropropan-2-yl)-[1,2,4]triazolo[1,5-a]pyrimidin-7-amine, reverse-phase HPLC purification of the crude product (105 mg) afforded the title compound as a colorless solid (43.1 mg, 0.093 mmol, 35% yield): $^1$H NMR (500 MHz, DMSO-d$_6$) δ 8.29 (s, 2 H), 6.81 (dd, J=2.8, 9.4 Hz, 2 H), 5.84-5.78 (m, 1 H), 4.14 (t, J=5.4 Hz, 2H), 3.02 (t, J=6.8 Hz, 2 H), 2.56 (bs, 3 H), 2.06 (bm, 2 H), 1.28 (d, J=6.7 Hz, 3H) ppm; HRMS (ESI$^+$) calculated for $C_{18}H_{19}N_6OF_5Cl$ [M+H$^+$] 465.1229, found 465.1230.

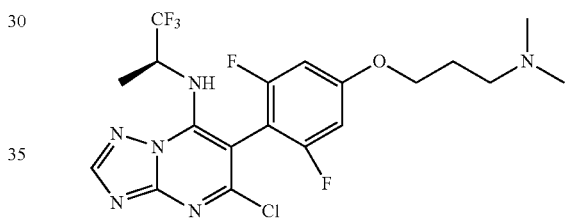

(S)-5-Chloro-6-(4-(3-(dimethylamino)propoxy)-2,6-difluorophenyl)-N-(1,1,1-trifluoropropan-2-yl)-[1,2,4]triazolo[1,5-a]pyrimidin-7-amine Following General Procedure B using 3-dimethylamino-1-propanol and (S)-5-chloro-6-(2,4,6-trifluorophenyl)-N-(1,1,1-trifluoropropan-2-yl)-[1,2,4]triazolo[1,5-a]pyrimidin-7-amine, reverse-phase HPLC purification afforded the title compound as a colorless, hygroscopic solid (9.2 mg, 0.019 mmol, 38% yield): $^1$H NMR (500 MHz, DMSO-d$_6$) δ 8.51 (bs, 1H), 8.18 (s, 1H), 6.89 (dd, J=4.0, 9.9 Hz, 2 H), 5.89-5.83 (m, 1 H), 4.10 (t, J=6.3 Hz, 2 H), 2.55 (t, J=7.6 Hz, 2 H), 2.29 (s, 6 H), 1.93 (p, J=6.8 Hz, 2 H), 1.37 (d, J=6.8 Hz, 3 H) ppm; HRMS (ESL) calculated for $C_{19}H_{21}N_6OF_5Cl$ [M+H$^+$] 479.1386, found 479.1384.

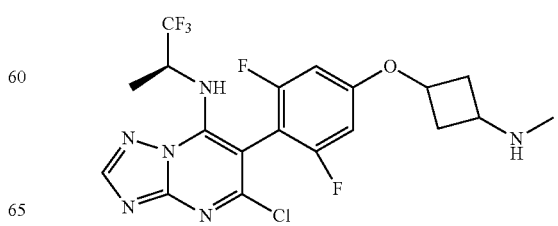

(S)-5-Chloro-6-(2,6-difluoro-4-(3-(methylamino)cyclobutoxy)phenyl)-N-(1,1,1-trifluoropropan-2-yl)-[1,2,4]triazolo[1,5-a]pyrimidin-7-amine Following General Procedure B using 3-(methylamino)-1-cyclobutanol (2.5:1 cis/trans isomers) and (S)-5-chloro-6-(2,4,6-trifluorophenyl)-N-(1,1,1-trifluoropropan-2-yl)-[1,2,4]triazolo[1,5-a]pyrimidin-7-amine, reverse-phase HPLC purification afforded the title compound as a light yellow, hygroscopic solid (8.9 mg, 0.019 mmol, 33% yield) as a 2.5:1 mixture of cis/trans isomers: $^1$H NMR (500 MHz, DMSO-$d_6$) major isomer δ 8.35 (bs, 1 H), 8.23 (s, 1 H), 6.74 (dd, J=4.2, 9.7 Hz, 2 H), 5.85-5.79 (m, 1 H), 4.59 (pent, J=7.0 Hz, 1 H), 3.16 (pent, J=7.7 Hz, 1 H), 2.89-2.84 (m, 2 H), 2.39 (s, 3 H), 2.11-2.06 (m, 2 H), 1.30 (d, J=6.7 Hz, 3 H); minor isomer (distinctive signals) δ 6.69-6.71 (m, 2 H), 4.96-4.93 (m, 1 H), 3.62-3.59 (m, 1 H), 2.40 (s, 3 H); HRMS (ESI) calculated for $C_{19}H_{19}N_6OF_5Cl$ [M+H$^+$] 477.1229, found 477.1221.

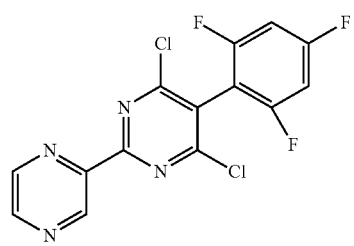 [SMILES: Fc1cc(F)c(-c2c(Cl)nc(-c3cnccn3)nc2Cl)c(F)c1]

4,6-Dichloro-2-(pyrazin-2-yl)-5-(2,4,6-trifluorophenyl)pyrimidine

A mixture of diethyl 2-(2,4,6-trifluorophenyl)malonate (250 mg, 0.861 mmol), 2-pyrazinecarboxamidine hydrochloride (144 mg, 0.904 mmol, 1.05 equiv), and tributylamine (221 μL [172 mg], 1.08 equiv) was stirred under nitrogen atmosphere at 180° C. for 1 h in a sealed tube. The mixture was cooled to room temperature and treated with 1.0 N hydrochloric acid. The precipitates were collected by filtration, washed with water and dried to give 2-pyrazin-2-yl-5-(2,4,6-trifluorophenyl)pyrimidine-4,6-diol as a dark tan solid (163 mg), which was used directly in the next step.

A mixture of 2-pyrazin-2-yl-5-(2,4,6-trifluorophenyl)pyrimidine-4,6-diol (163 mg) in phosphorous oxychloride (2.03 mL, 21.9 mmol, 43 equiv) and 2,6-lutidine (404 μL, 3.51 mmol, 6.9 equiv) was heated at 110° C. for 16 h in a sealed tube. The excess phosphorous oxychloride was removed in vacuo, and the resulting residue was dissolved in ethyl acetate. The organic layer was washed with water and saturated sodium chloride, dried over sodium sulfate, and concentrated. The residue was purified by silica gel chromatography over silica gel, eluting with a gradient of 20% ethyl acetate in hexanes to 33% ethyl acetate in hexanes. Concentration provided 104 mg of the title compound as a light yellow solid (32% over two steps).

$^1$H-NMR (500 MHz; CDCl$_3$): δ 9.73 (s, 1H), 8.84 (s, 1H), 8.77 (s, 1H), 6.88-6.84 (m, 2H) ppm.

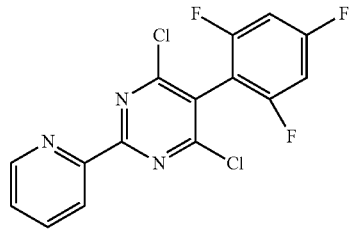 [SMILES: Fc1cc(F)c(-c2c(Cl)nc(-c3ccccn3)nc2Cl)c(F)c1]

4,6-Dichloro-2-(pyridin-2-yl)-5-(2,4,6-trifluorophenyl)pyrimidine

Prepared as 4,6-Dichloro-2-(pyrazin-2-yl)-5-(2,4,6-trifluorophenyl)pyrimidine from picolinimidamide hydrochloride and 2-(2,4,6-trifluorophenyl)malonate. Yield: 58% over two steps.

$^1$H-NMR (500 MHz; CDCl$_3$): δ 9.16 (d, J=5.4 Hz, 1H), 9.00-8.98 (m, 1H), 8.78 (td, J=7.9, 1.2 Hz, 1H), 8.36 (t, J=6.7 Hz, 1H), 6.88 (dd, J=8.4, 7.5 Hz, 2H) ppm.

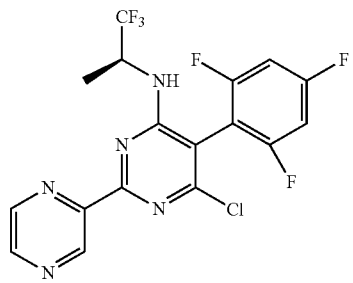 [SMILES: C[C@H](Nc1nc(-c2cnccn2)nc(Cl)c1-c1c(F)cc(F)cc1F)C(F)(F)F]

(S)-6-chloro-2-(pyrazin-2-yl)-5-(2,4,6-trifluorophenyl)-N-(1,1,1-trifluoropropan-2-yl)pyrimidin-4-amine (CNDR-51549)

A mixture of 4,6-Dichloro-2-(pyrazin-2-yl)-5-(2,4,6-trifluorophenyl)pyrimidine (71 mg, 0.199 mmol), (S)-2,2,2-trifluoro-1-methylethylamine (68 μL, [78 mg] 0.696 mmol, 3.5 equiv), and in N,N-dimethylformamide (1.73 mL, 22.5 mmol) was stirred at 90° C. in a sealed tube for 18 h. The reaction mixture was partitioned between ethyl acetate and saturated sodium chloride. The organic layer was washed with saturated sodium chloride (3×), dried over sodium sulfate, and concentrated. The residue was purified by silica gel chromatography, using gradients of ethyl acetate in hexanes. Concentration provided the desired compound as a white solid. Yield: 18% $^1$H-NMR (500 MHz; DMSO-$d_6$): δ 9.57 (d, J=1.4 Hz, 1H), 8.85-8.83 (m, 2H), 7.70 (d, J=8.8 Hz, 1H), 7.48-7.42 (m, 2H), 5.52 (tt, J=13.6, 6.7 Hz, 1H), 1.35 (d, J=7.1 Hz, 3H) ppm. HRMS ESI$^+$: calculated for $C_{17}H_{11}ClF_6N_5$ 434.0607, found 434.0616.

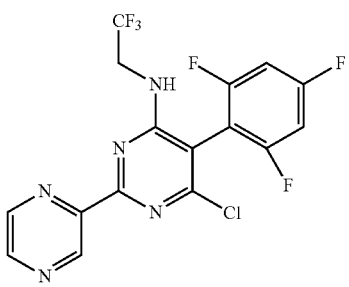 [SMILES: Fc1cc(F)c(-c2c(Cl)nc(-c3cnccn3)nc2NCC(F)(F)F)c(F)c1]

6-Chloro-2-(pyrazin-2-yl)-N-(2,2,2-trifluoroethyl)-5-(2,4,6-trifluorophenyl)pyrimidin-4-amine (CNDR-51550)

Prepared as CNDR-51549 from 4,6-Dichloro-2-(pyrazin-2-yl)-5-(2,4,6-trifluorophenyl)pyrimidine and 2,2,2-trifluoroethylamine Yield: 31%.

$^1$H-NMR (500 MHz; CDCl$_3$): δ 9.65 (d, J=1.4 Hz, 1H), 8.79 (dd, J=2.4, 1.5 Hz, 1H), 8.72 (d, J=2.4 Hz, 1H), 6.89-6.85 (m, 2H), 5.21-5.18 (m, 1H), 4.37 (qd, J=8.7, 6.6 Hz, 2H) ppm.

HRMS [ESI]$^+$: calculated for C$_{16}$H$_9$ClF$_6$N$_5$ 420.0451; found: 420.0459.

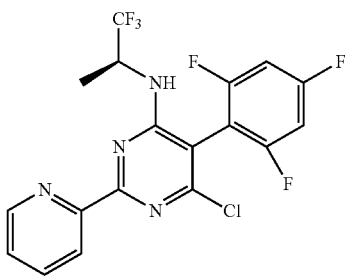 [SMILES: C[C@H](Nc1nc(-c2ccccn2)nc(Cl)c1-c1c(F)cc(F)cc1F)C(F)(F)F]

(S)-6-chloro-2-(pyridin-2-yl)-5-(2,4,6-trifluorophenyl)-N-(1,1,1-trifluoropropan-2-yl)pyrimidin-4-amine (CNDR-51552)

Prepared as CNDR-51549 from 4,6-Dichloro-2-(pyridin-2-yl)-5-(2,4,6-trifluorophenyl)pyrimidine and (S)-2,2,2-trifluoro-1-methylethylamine.

$^1$H-NMR (500 MHz; CDCl$_3$): δ 8.86 (d, J=4.6 Hz, 1H), 8.43 (d, J=7.9 Hz, 1H), 7.90-7.87 (m, 1H), 7.44 (dd, J=7.2, 5.0 Hz, 1H), 6.92-6.86 (m, 2H), 5.41-5.35 (m, 1H), 4.60 (d, J=9.3 Hz, 1H), 1.41 (d, J=7.0 Hz, 3H) ppm.

HRMS [ESI]$^-$: calculated for C$_{18}$H$_{10}$ClF$_6$N$_4$ 431.0498; found: 431.0508.

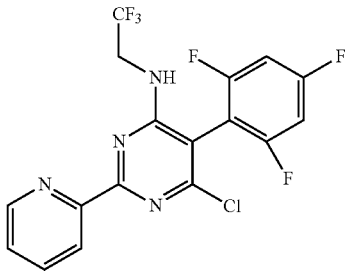 [SMILES: Fc1cc(F)c(-c2c(Cl)nc(-c3ccccn3)nc2NCC(F)(F)F)c(F)c1]

6-Chloro-2-(pyridin-2-yl)-N-(2,2,2-trifluoroethyl)-5-(2,4,6-trifluorophenyl)pyrimidin-4-amine (CNDR-51553)

Prepared as CNDR-51549 from 4,6-Dichloro-2-(pyridin-2-yl)-5-(2,4,6-trifluorophenyl)pyrimidine and (S)-2,2,2-trifluoroethylamine Yield 12%.

$^1$H-NMR (500 MHz; CDCl$_3$): δ 8.83 (d, J=4.0 Hz, 1H), 8.43 (d, J=7.9 Hz, 1H), 7.88 (t, J=7.3 Hz, 1H), 7.44 (t, J=5.8 Hz, 1H), 6.84-6.81 (m, 2H), 5.04 (t, J=6.0 Hz, 1H), 4.38 (dd, J=15.4, 8.0 Hz, 2H) ppm.

HRMS [ESI]$^+$: calculated for C$_{17}$H$_{10}$ClF$_6$N$_4$ 419.0498; found: 419.0496.

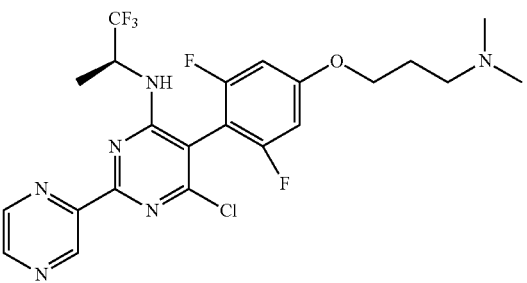 [SMILES: C[C@H](Nc1nc(-c2cnccn2)nc(Cl)c1-c1c(F)cc(OCCCN(C)C)cc1F)C(F)(F)F]

(S)-6-Chloro-5-(4-(3-(dimethylamino)propoxy)-2,6-difluorophenyl)-2-(pyrazin-2-yl)-N-(1,1,1-trifluoropropan-2-yl)pyrimidin-4-amine (CNDR-51554)

To a solution of CNDR-51549 (27 mg, 0.062 mmol) and 3-(dimethylamino)propan-1-ol (38 μL, 0.321 mmol) in dimethylsulfoxide (322 mL) was added sodium hydride (60% in mineral oil, 13 mg, 0.321 mmol) at room temperature. The reaction mixture was stirred at 60° C. for 2 h, cooled to room temperature, dissolved in additional DMSO, filtered, and purified by preparative reverse phase HPLC. Concentration provided the title compound as a white solid. Yield: 8%.

$^1$H-NMR (500 MHz; DMSO-d$_6$): δ 9.58 (d, J=1.2 Hz, 1H), 8.86-8.84 (m, 2H), 7.70 (d, J=8.8 Hz, 1H), 6.95 (t, J=10.0 Hz, 2H), 5.53 (dd, J=15.3, 7.6 Hz, 1H), 4.12 (t, J=6.2 Hz, 2H), 2.38 (t, J=7.1 Hz, 2H), 2.17 (s, 6H), 1.90 (quintet, J=6.7 Hz, 2H), 1.36 (d, J=7.1 Hz, 3H) ppm.

HRMS [ESI]$^+$: calculated for C$_{22}$H$_{23}$ClF$_5$N$_6$O, 517.1542; found: 517.1536.

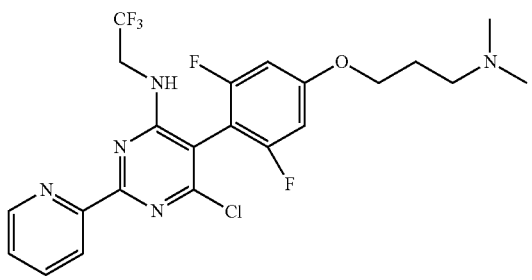 [SMILES: CN(C)CCCOc1cc(F)c(-c2c(Cl)nc(-c3ccccn3)nc2NCC(F)(F)F)c(F)c1]

6-Chloro-5-(4-(3-(dimethylamino)propoxy)-2,6-difluorophenyl)-2-(pyridin-2-yl)-N-(2,2,2-trifluoroethyl)pyrimidin-4-amine (CNDR-51557)

Prepared as CNDR-51554 from (S)-6-chloro-2-(pyridin-2-yl)-5-(2,4,6-trifluorophenyl)-N-(1,1,1-trifluoropropan-2-yl)pyrimidin-4-amine (CNDR-51552) and 3-(dimethylamino)propan-1-ol.

¹H-NMR (500 MHz; MeOD): δ 8.72 (dd, J=4.7, 0.7 Hz, 1H), 8.54-8.52 (m, 1H), 8.03 (td, J=7.8, 1.7 Hz, 1H), 7.58 (ddd, J=7.5, 4.9, 1.0 Hz, 1H), 6.79 (d, J=9.3 Hz, 2H), 4.38 (q, J=9.1 Hz, 2H), 4.14 (t, J=6.0 Hz, 2H), 2.73 (t, J=7.6 Hz, 2H), 2.45 (s, 6H), 2.07 (dd, J=13.9, 7.3 Hz, 2H) ppm.

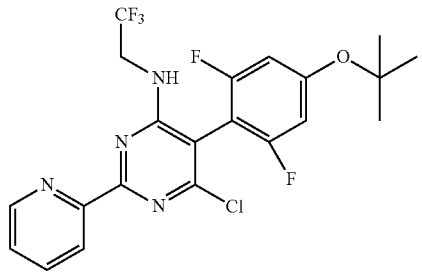 [SMILES: CC(C)(C)Oc1cc(F)c(-c2c(Cl)nc(-c3ccccn3)nc2NCC(F)(F)F)c(F)c1]

5-(4-(tert-butoxy)-2,6-difluorophenyl)-6-chloro-2-(pyridin-2-yl)-N-(2,2,2-trifluoroethyl)pyrimidin-4-amine (CNDR-51560)

To a solution of 6-Chloro-2-(pyridin-2-yl)-N-(2,2,2-trifluoroethyl)-5-(2,4,6-trifluorophenyl)-pyrimidin-4-amine (14 mg, 0.0334 mmol) in THF (198 μl), potassium tert-butoxide (1M THF solution, 66.9 μl) was added at room temperature. The reaction mixture was stirred for 1 h at room temperature and then partitioned between water and DCM. The combined organic layers were washed with brine, dried over sodium sulfate, filtered and concentrated in vacuo. Purification by silica gel preparative TLC using 20% ethyl acetate in hexanes as eluent, furnished the desired product.

¹H-NMR (500 MHz; CDCl₃): δ 8.91 (s, 1H), 8.51-8.50 (m, 1H), 7.95-7.94 (m, 1H), 7.50-7.48 (m, 1H), 6.72 (d, J=9.1 Hz, 2H), 4.99 (s, 1H), 4.45 (dt, J=2.0, 1.3 Hz, 2H), 1.49 (s, 9H) ppm.

HRMS [ESI]⁺: calculated for $C_{21}H_{19}ClF_5N_4O$, 473.1168; found: 473.1156.

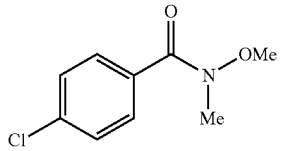 [SMILES: CON(C)C(=O)c1ccc(Cl)cc1]

4-Chloro-N-methoxy-N-methylbenzamide: Commercially available 4-chlorobenzoic acid (3.4913 g, 22.3 mmol, 1.00 equiv) was suspended in CH₂Cl₂ (30 mL) and cooled to 0° C. at which time Me(OMe)NH.HCl (2.39 g, 24.5 mmol, 1.10 equiv), N-methymorpholine (2.48 g, 2.70 mL, 24.5 mmol, 1.10 equiv), and N-(3-Dimethylaminopropyl)-N'-ethylcarbodiimide hydrochloride (4.70 g, 24.5 mmol, 1.10 equiv) were added sequentially. After stirring for 12 h the reaction was quenched with NH₄Cl (sat. aq.) and the layers were separated. The aqueous layer was back extracted with CH₂Cl₂ (3×). The combined organic layers were washed with H₂O, brine, dried over Na₂SO₄, filtered and concentrated. The crude residue was purified via Silica gel flash chromatography (1:1 EtOAc/Hex) to give 3.929 g (88%) of the title compound as a clear oil. The spectral data was identical to that reported in the literature[IV]: ¹H NMR (500 MHz, CDCl₃) δ 7.68-7.54 (m, 2H), 7.40-7.29 (m, 2H), 3.49 (s, 3H), 3.31 (s, 3H) ppm.

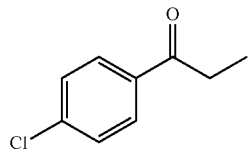

1-(4-chlorophenyl)Propan-1-one: 4-Chloro-N-methoxy-N-methylbenzamide (0.5352 g, 2.68 mmol, 1.00 equiv) was dissolved in Et₂O (10 mL) and cooled to 0° C. Ethylmagnesium bromide (1.80 mL, 5.36 mmol, 2.00 equiv, 3M solution in Et₂O) was added dropwise. After stirring for 3 h the reaction was quenched with NH₄Cl (sat. aq.) and the layers were separated. The aqueous layer was back extracted with Et₂O (3×). The combined organic layers were washed with H₂O, brine, dried over Na₂SO₄, filtered and concentrated. Purification by silica gel column chromatography using a 1:1 mixture of ethyl acetate in hexanes as eluant furnished the title compound (0.349 g) as a clear oil. Yield: 77%. The spectral data was identical to that reported in the literature[V]. ¹H NMR (500 MHz, CDCl₃): δ 7.94-7.89 (m, 2H), 7.49-7.38 (m, 2H), 2.97 (q, J=7.2 Hz, 2H), 1.22 (t, J=7.2 Hz, 3H) ppm.

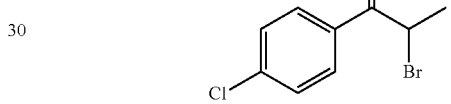

2-Bromo-1-(4-chlorophenyl)propan-1-one: 1-(4-chlorophenyl)Propan-1-one (0.2264 g, 1.34 mmol, 1.00 equiv) was dissolved in acetic acid (4 mL) and 1 drop of HBr (48%) was added. Bromine (0.225 g, 0.08 mL, 1.05 equiv) was added dropwise. After 1 h the reaction was carefully quenched with NaHCO₃ (sat. aq.) and extracted with ethyl acetate (3×). The combined organic layers were washed with brine, dried over Na₂SO₄ and concentrated under reduced pressure. The crude residue was purified via silica gel flash chromatography (25% EtOAc/Hex) to give 0.2897 g (87%) of the title compound as an orange oil. The spectral data was identical to that reported in the literature[VI]: ¹H NMR (500 MHz, CDCl₃): δ 7.99-7.94 (m, 2H), 7.49-7.40 (m, 2H), 5.25 (q, J=6.6 Hz, 1H), 1.91 (s, 3H) ppm.

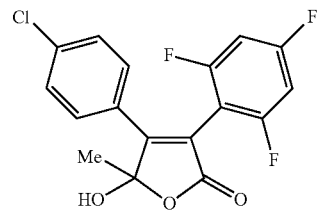 [SMILES: CC1(O)OC(=O)C(c2c(F)cc(F)cc2F)=C1c1ccc(Cl)cc1]

4-(4-chlorophenyl)-5-Hydroxy-5-methyl-3-(2,4,6-trifluorophenyl)furan-2(5H)-one: 2-Bromo-1-(4-chlorophenyl)propan-1-one (0.1783 g, 0.61 mmol, 1.00 equiv) and 2,4,6-trifluorophenylacetic acid (0.245 g, 1.29 mmol, 1.10 equiv) were dissolved in CH₃CN (2 mL). Triethylamine (0.130 g, 0.18 mL, 1.29 mmol, 1.10 equiv) was added dropwise and allowed to stir for 12 h. DBU (0.445 g, 0.44 mL, 2.93 mmol, 2.50 equiv) was added dropwise and the resulting dark mixture was allowed to stir for 1 h. Air was then bubbled through the mixture for 5 h. The reaction was quenched with NH$_4$Cl (sat. aq.) and extracted with ethyl acetate (3×). The combined organic extracts were washed with NaHCO$_3$ (sat. aq.), brine, dried over Na$_2$SO$_4$, filtered and concentrated. The crude residue was purified via silica gel flash chromatography (20% EtOAc/Hex) to give 0.199 g (48%) of the title compound as a clear oil: $^1$H NMR (500 MHz, CDCl$_3$) δ 7.50-7.45 (m, 2H), 7.34-7.27 (m, 2H), 6.80 (tt, J=9.0, 2.1 Hz, 1H), 6.58 (tt, J=9.0, 2.1 Hz, 1H), 5.24 (s, 1H), 1.73 (s, 3H) ppm.

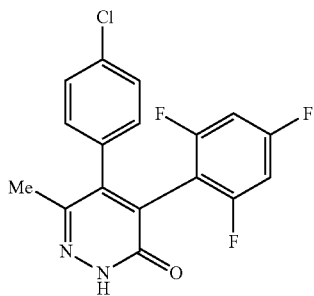 [SMILES: Cc1n[nH]c(=O)c(-c2c(F)cc(F)cc2F)c1-c1ccc(Cl)cc1]

5-(4-chlorophenyl)-6-Methyl-4-(2,4,6-trifluorophenyl)pyridazin-3(2H)-one: 4-(4-chlorophenyl)-5-Hydroxy-5-methyl-3-(2,4,6-trifluorophenyl)furan-2(5H)-one (0.141 g, 0.4 mmol, 1.00 equiv) was dissolved in 1-butanol (2.5 mL). Hydrazine hydrate (0.04 g, 0.03 mL, 0.68 mmol, 1.70 equiv) was added dropwise and heated to 120° C. for 24 h. Upon cooling the reaction mixture was placed in the refrigerator overnight. The precipitated solid was collected and washed with hexanes to give the title compound as a white solid: $^1$H NMR (500 MHz, CDCl$_3$) δ 11.40 (bs, 1H), 7.34-7.28 (m, 2H), 7.07-7.00 (m, 2H), 6.57 (dd, J=8.7, 7.2 Hz, 2H), 2.11 (s, 3H) ppm; $^{13}$C NMR (126 MHz, CDCl$_3$) δ 159.86, 147.46, 144.87, 135.21, 133.26, 129.08, 129.00, 100.69 (d, J=25.2 Hz), 20.91 ppm.

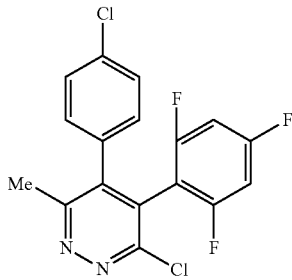 [SMILES: Cc1nnc(Cl)c(-c2c(F)cc(F)cc2F)c1-c1ccc(Cl)cc1]

3-chloro-5-(4-chlorophenyl)-6-methyl-4-(2,4,6-trifluorophenyl)pyridazine: 5-(4-chlorophenyl)-6-Methyl-4-(2,4,6-trifluorophenyl)pyridazin-3(2H)-one (0.0295 g, 0.084 mmol, 1.00 equiv) was dissolved in POCl$_3$ (1 mL) and heated 110° C. for 1 h. After cooling, the mixture was concentrated under reduced pressure. The crude material was taken up in EtOAc and washed with H$_2$O, brine, dried over Na$_2$SO$_4$, and concentrated under reduced pressure. The crude residue was purified via silica gel flash chromatography (40% EtOAc/Hex) to give 0.0311 g (64%) of the title compound as a pale yellow oil: $^1$H NMR (500 MHz, CDCl$_3$) δ 7.36-7.28 (m, 2H), 7.06-6.96 (m, 2H), 6.68-6.56 (m, 2H), 2.53 (s, 3H) ppm; $^{13}$C NMR (126 MHz, CDCl$_3$) δ 158.60, 155.55, 142.73, 135.49, 132.70, 129.26, 129.05, 128.15, 100.91 (d, J=26.2 Hz), 21.35 ppm.

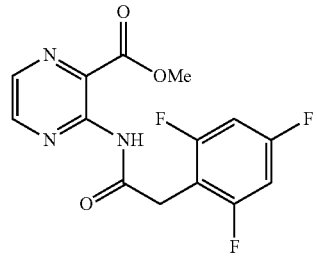 [SMILES: COC(=O)c1nccnc1NC(=O)Cc1c(F)cc(F)cc1F]

Methyl 3-(2-(2,4,6-trifluorophenyl)acetamido)pyrazine-2-carboxylate: 2,4,6-Trifluorophenylacetic acid (0.4710 g, 2.48 mmol, 1.00 equiv) was dissolved in CH$_2$Cl$_2$ (4 mL) and two drops of DMF was added. Oxalyl chloride (0.377 g, 0.26 mL, 2.97 mmol, 1.20 equiv) was added dropwise and stirred for 30 minutes at room temperature. The solution was heated to reflux and stirred for 2 h. After cooling to room temperature the crude acid chloride was used directly in the next step without purification. The reaction mixture containing the acid chloride in CH$_2$Cl$_2$ (4 mL) was added dropwise to a solution containing methyl 3-aminopyrazine-2-carboxylate (0.3794 g, 2.48 mmol, 1.00 equiv), pyridine (0.372 g, 0.38 mL, 4.71 mmol, 1.90 equiv), and DMAP (catalytic quantities). The reaction mixture was stirred for 20 h and then diluted with CH$_2$Cl$_2$ (100 mL) and washed with water, 1 N HCl, and brine. The organic layers was dried over Na$_2$SO$_4$, concentrated under reduced pressure, and purified via silica gel flash chromatography to deliver 0.2362 g (29%) of the title compound as an orange solid. The spectral data was identical to that reported in the literature. $^1$H NMR (500 MHz, CDCl$_3$) δ 10.82 (s, 1H), 8.59 (d, J=2.3 Hz, 1H), 8.41 (d, J=2.3 Hz, 1H), 6.73 (dd, J=8.7, 7.3 Hz, 2H), 4.03 (s, 5H) ppm.

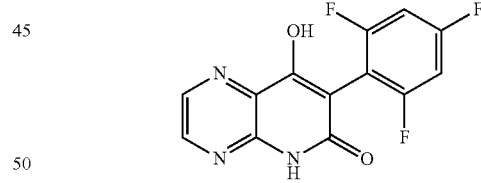

8-Hydroxy-7-(2,4,6-trifluorophenyl)pyrido[2,3-b]pyrazin-6(5H)-one: Methyl 3-(2-(2,4,6-trifluorophenyl)acetamido)pyrazine-2-carboxylate (0.2239 g, 0.69 mmol, 1.00 equiv) and anhydrous K$_2$CO$_3$ (0.1903 g, 1.38 mmol, 2.00 equiv) were suspended in DMF (4 mL) and heated to 80° C. for 3 h. After cooling to room temperature the mixture was poured into ice-cold water, acidified to a pH of 3 with 1 N HCl, and extracted with EtOAc (3×). The combined organic layers were washed with brine, dried over Na$_2$SO$_4$, filtered, and concentrated under reduced pressure to give 0.1783 g (88%) of the title compound as a yellow powder. The spectral data was identical to that reported in the literature.[VII] $^1$H NMR (500 MHz, DMSO-d$_6$) δ 10.80 (s, 1H), 8.70 (d, J=2.3 Hz, 1H), 8.56 (d, J=2.3 Hz, 1H), 7.22 (m, 2H) ppm.

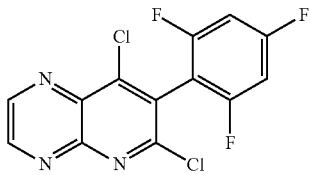 [SMILES: Fc1cc(F)c(-c2c(Cl)nc3nccnc3c2Cl)c(F)c1]

6,8-Dichloro-7-(2,4,6-trifluorophenyl)pyrido[2,3-b]pyrazine: 8-Hydroxy-7-(2,4,6-trifluorophenyl)pyrido[2,3-b]pyrazin-6(5H)-one (0.1783 g, 0.61 mmol, 1.00 equiv) and DMF (0.089 g, 0.095 mL, 1.22 mmol, 2.00 equiv) were dissolved in DCE (5 mL) and heated to 80° C. POCl$_3$ (0.373 g, 0.23 mL, 2.43 mmol, 4.00 equiv) was added dropwise at this temperature. After the addition, the reaction was stirred for 3 h allowing the temperature to cool to room temperature. 50 mL of NaHCO$_3$ (sat. aq.) was added and the solution was stirred for 30 min. The reaction mixture was then extracted with EtOAc (3×) and the combined organic layers were washed with brine, dried over Na$_2$SO$_4$, filtered, and concentrated under reduced pressure. The spectral data was identical to that reported in the literature.[VII] $^1$H NMR (500 MHz, CDCl$_3$) δ 9.17 (d, J=2.1 Hz, 1H), 9.11 (d, J=2.1 Hz, 1H), 6.86 (dd, J=8.6, 7.6 Hz, 2H) ppm.

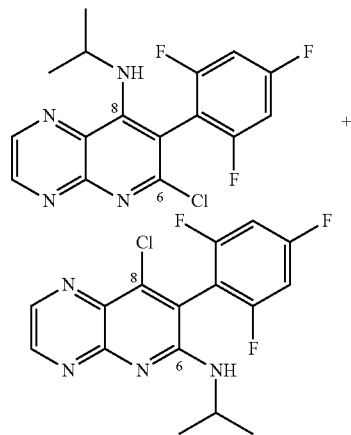

6-Chloro-N-isopropyl-7-(2,4,6-trifluorophenyl)pyrido[2,3-b]pyrazin-8-amine and 8-chloro-N-isopropyl-7-(2,4,6-trifluorophenyl)pyrido[2,3-b]pyrazin-6-amine: 6,8-Dichloro-7-(2,4,6-trifluorophenyl)pyrido[2,3-b]pyrazine (0.1616 g, 0.49 mmol, 1.00 equiv) and DMAP (0.022 g, 0.09 mmol, 0.19 equiv) were dissolved in DMF (2 mL). Anhydrous potassium carbonate (0.346 g, 2.51 mmol, 1.55 equiv) and isopropylamine (0.148 g, 0.21 mL, 2.51 mmol, 1.55 equiv) were added consecutively and the mixture was allowed to stir for 24 h at room temperature. The reaction was poured into ice water and extracted with EtOAc (3×). The combined organic extracts were washed with brine, dried over Na$_2$SO$_4$, filtered, and concentrated under reduced pressure. Purification by silica gel preparative thin layer chromatography using a 1:1 mixture of ethyl acetate in hexanes as eluent furnished the title compound and 8-chloro-N-isopropyl-7-(2,4,6-trifluorophenyl)pyrido[2,3-b]pyrazin-6-amine. The spectral data of both compounds were identical to that reported in the literature.[VII] C-8 alkylated pyridopyrazine: $^1$H NMR (500 MHz, CDCl$_3$) δ 8.99 (d, J=1.9 Hz, 1H), 8.66 (d, J=1.8 Hz, 1H), 6.93 (bs, 1H), 6.83 (dd, J=8.6, 7.6 Hz, 2H), 3.36 (m, 1H), 1.11 (d, J=6.3 Hz, 6H) ppm. C-6 alkylated pyridopyrazine: $^1$H NMR (500 MHz, CDCl$_3$) δ 8.84 (d, J=2.0 Hz, 1H), 8.63 (d, J=2.0 Hz, 1H), 6.93 (dd, J=8.6, 6.9 Hz, 2H), 4.72-4.60 (m, 1H), 4.54 (s, 1H), 1.24 (d, J=6.5 Hz, 6H) ppm.

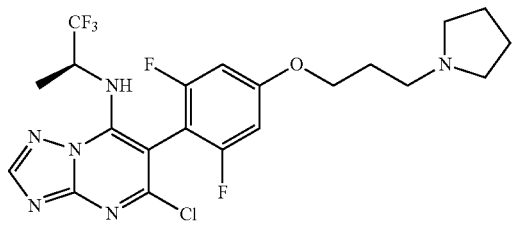 [SMILES: C[C@H](Nc1c(-c2c(F)cc(OCCCN3CCCC3)cc2F)c(Cl)nc2ncnn12)C(F)(F)F]

(S)-5-Chloro-6-(2,6-difluoro-4-(3-(pyrrolidin-1-yl)propoxy)phenyl)-N-(1,1,1-trifluoropropan-2-yl)-[1,2,4]triazolo[1,5-a]pyrimidin-7-amine (CNDR-51569)

Following General Procedure B using 3-(pyrrolidin-1-yl)propan-1-ol and (S)-5-chloro-6-(2,4,6-trifluorophenyl)-N-(1,1,1-trifluoropropan-2-yl)-[1,2,4]triazolo[1,5-a]pyrimidin-7-amine, reverse-phase HPLC purification afforded the title compound as formic acid salt. Yield: 35%.

$^1$H-NMR (500 MHz; CDCl$_3$): δ 12.42 (s, 1H), 8.36 (s, 1H), 6.60 (d, J=9.1 Hz, 2H), 5.92 (d, J=10.2 Hz, 1H), 4.97 (broad s, 1H), 4.13 (t, J=5.5 Hz, 2H), 3.89 (m, 2H), 3.80-3.78 (m, 2H), 3.34 (m, 2H), 2.86 (m, 2H), 2.33 (m, 2H), 2.16 (m, 2H), 1.39 (d, J=6.8 Hz, 3H) ppm. HRMS (ESI$^+$) calculated for C$_2$M$_{23}$ClF$_5$N$_6$O [M+H$^+$]: 505.1542, found 505.1524.

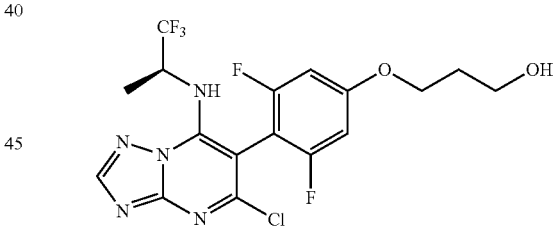

(S)-3-(4-(5-chloro-7-((1,1,1-trifluoropropan-2-yl)amino)-[1,2,4]Triazolo[1,5-a]pyrimidin-6-yl)-3,5-difluorophenoxy)propan-1-ol (CNDR-51567)

Following General Procedure B using propane-1,3-diol and (S)-5-chloro-6-(2,4,6-trifluorophenyl)-N-(1,1,1-trifluoropropan-2-yl)-[1,2,4]triazolo[1,5-c]pyrimidin-7-amine, reverse-phase HPLC purification afforded the title compound. Yield: 60%.

$^1$H-NMR (500 MHz; CDCl$_3$): δ 8.40 (s, 1H), 6.70-6.67 (m, 2H), 5.91 (d, J=8.7 Hz, 1H), 4.77 (broad s, 1H), 4.21 (t, J=6.1 Hz, 2H), 3.91 (t, J=5.9 Hz, 2H), 2.18-2.09 (m, 2H), 1.70 (s, 1H), 1.42 (d, J=6.8 Hz, 3H) ppm. HRMS (ESL) calculated for C$_{17}$H$_{16}$ClF$_5$N$_5$O$_2$ [M+H$^+$]: 452.0913, found 452.0902.

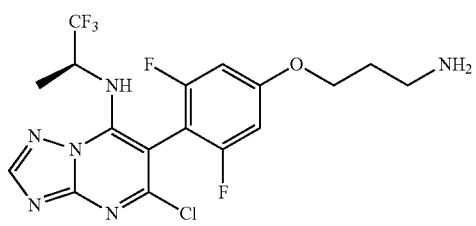 [SMILES: C[C@H](Nc1c(-c2c(F)cc(OCCCN)cc2F)c(Cl)nc2ncnn12)C(F)(F)F]

(S)-6-(4-(3-aminopropoxy)-2,6-difluorophenyl)-5-Chloro-N-(1,1,1-trifluoropropan-2-yl)-[1,2,4]triazolo[1,5-a]pyrimidin-7-amine (CNDR-51570)

Following General Procedure B using 3-aminopropan-1-ol and (S)-5-chloro-6-(2,4,6-trifluorophenyl)-N-(1,1,1-trifluoropropan-2-yl)-[1,2,4]triazolo[1,5-c]pyrimidin-7-amine, reverse-phase HPLC purification afforded the title compound as formic acid salt. Yield: 22%.

$^1$H-NMR (500 MHz; DMSO-$d_6$): δ 8.30 (s, 1H), 8.09 (d, J=0.3 Hz, 1H), 6.76-6.74 (m, 2H), 5.78 (broad s, 1H), 4.13 (t, J=5.9 Hz, 2H), 3.36 (broad s, 2H), 2.98 (t, J=7.2 Hz, 2H), 2.03 (t, J=6.6 Hz, 2H), 1.21 (d, J=6.5 Hz, 3H) ppm. HRMS (ESI) calculated for $C_{17}H_{17}ClF_5N_6$ [M+H$^+$]: 451.1073, found 451.1076.

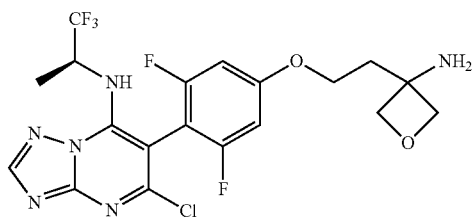 [SMILES: C[C@H](Nc1c(-c2c(F)cc(OCCC3(N)COC3)cc2F)c(Cl)nc2ncnn12)C(F)(F)F]

(S)-6-(4-(2-(3-aminooxetan-3-yl)ethoxy)-2,6-Difluorophenyl)-5-chloro-N-(1,1,1-trifluoropropan-2-yl)-[1,2,4]triazolo[1,5-a]pyrimidin-7-amine (CNDR-51572)

Following General Procedure B using 2-(1-aminocyclobutyl)ethan-1-ol and (S)-5-chloro-6-(2,4,6-trifluorophenyl)-N-(1,1,1-trifluoropropan-2-yl)-[1,2,4]triazolo[1,5-a]pyrimidin-7-amine, reverse-phase HPLC purification afforded the title compound as trifluoroacetic acid salt. Yield: 44%. HRMS (ESI$^+$) calculated for $C_{19}H_{19}ClF_5N_6O_2$ [M+H$^+$] 493.1178, found 493.1177.

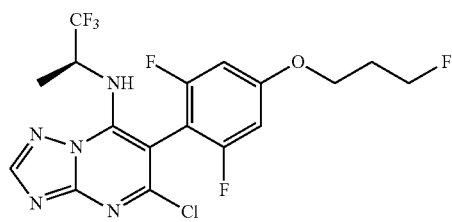 [SMILES: C[C@H](Nc1c(-c2c(F)cc(OCCCF)cc2F)c(Cl)nc2ncnn12)C(F)(F)F]

(S)-5-Chloro-6-(2,6-difluoro-4-(3-fluoropropoxy)phenyl)-N-(1,1,1-trifluoropropan-2-yl)-[1,2,4]triazolo[1,5-a]pyrimidin-7-amine (CNDR-51588)

Following General Procedure B using 3-chloropropan-1-ol and (S)-5-chloro-6-(2,4,6-trifluorophenyl)-N-(1,1,1-trifluoropropan-2-yl)-[1,2,4]triazolo[1,5-a]pyrimidin-7-amine, reverse-phase HPLC purification afforded the title compound. Yield: 66%.

$^1$H-NMR (500 MHz; CDCl$_3$): δ 8.39 (s, 1H), 6.69-6.65 (m, 2H), 5.89 (d, J=9.2 Hz, 1H), 4.76 (m, 1H), 4.73 (t, J=5.6 Hz, 1H), 4.63 (t, J=5.6 Hz, 1H), 4.18 (t, J=6.1 Hz, 2H), 2.29-2.20 (m, 2H), 1.41 (d, J=6.8 Hz, 3H) ppm. HRMS (ESI$^+$) calculated for $C_{17}H_{15}N_5OF_6Cl$ [M+H$^+$]: 454.0864, found 454.0858.

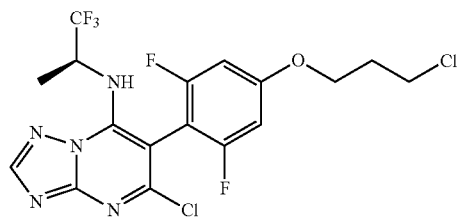 [SMILES: C[C@H](Nc1c(-c2c(F)cc(OCCCCl)cc2F)c(Cl)nc2ncnn12)C(F)(F)F]

(S)-5-Chloro-6-(4-(3-chloropropoxy)-2,6-difluorophenyl)-N-(1,1,1-trifluoropropan-2-yl)-[1,2,4]triazolo[1,5-a]pyrimidin-7-amine (CNDR-51591)

Following General Procedure B using 3-fluoropropan-1-ol and (S)-5-chloro-6-(2,4,6-trifluorophenyl)-N-(1,1,1-trifluoropropan-2-yl)-[1,2,4]triazolo[1,5-a]pyrimidin-7-amine, reverse-phase HPLC purification afforded the title compound. Yield: 86%.

$^1$H-NMR (500 MHz; CDCl$_3$): δ 8.41 (s, 1H), 6.68 (m, 2H), 5.89 (d, J=9.8 Hz, 1H), 4.79 (broad s, 1H), 4.21 (t, J=5.8 Hz, 2H), 3.79 (t, J=6.2 Hz, 2H), 2.32 (m, 2H), 1.43 (d, J=6.8 Hz, 3H) ppm. HRMS (ESI$^+$) calculated for $C_{17}H_{15}N_5OF_5Cl_2$ [M+H$^+$]: 470.0568, found 470.0578.

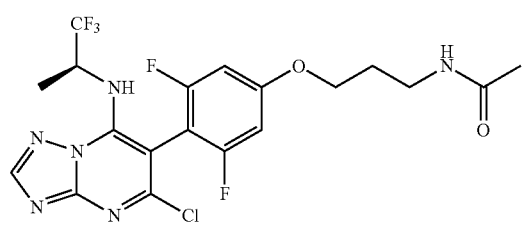 [SMILES: CC(=O)N(C)CCCOc1cc(F)c(-c2c(Cl)nc3ncnn3c2N[C@@H](C)C(F)(F)F)c(F)c1]

(S)—N-(3-(4-(5-chloro-7-((1,1,1-trifluoropropan-2-yl)amino)-[1,2,4]Triazolo[1,5-a]pyrimidin-6-yl)-3,5-difluorophenoxy)propyl)acetamide (CNDR-51589)

Following General Procedure B using N-(3-hydroxypropyl)acetamide and (S)-5-chloro-6-(2,4,6-trifluorophenyl)-N-(1,1,1-trifluoropropan-2-yl)-[1,2,4]triazolo[1,5-a]pyrimidin-7-amine, reverse-phase HPLC purification afforded the title compound. Yield: 90%.

$^1$H-NMR (500 MHz; CDCl$_3$): δ 8.37 (s, 1H), 6.64 (d, J=8.9 Hz, 2H), 6.11 (s, 1H), 5.98 (d, J=10.6 Hz, 1H), 4.85 (s, 1H), 4.10 (t, J=6.1 Hz, 2H), 3.48 (q, J=6.3 Hz, 2H), 2.08 (t, J=6.4 Hz, 2H), 2.01 (s, 3H), 1.42 (d, J=6.8 Hz, 3H) ppm. HRMS (ESI) calculated for $C_{19}H_{19}ClF_5N_6O_2$ [M+H$^+$]: 493.1178, found 493.1180.

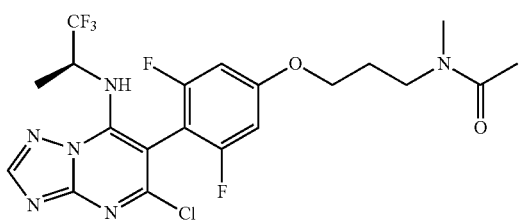

(S)—N-(3-(4-(5-chloro-7-((1,1,1-trifluoropropan-2-yl)amino)-[1,2,4]Triazolo[1,5-a]pyrimidin-6-yl)-3,5-difluorophenoxy)propyl)-N-methylacetamide (CNDR-51593)

Following General Procedure B using N-(3-hydroxypropyl)-N-methylacetamide and (S)-5-chloro-6-(2,4,6-trifluorophenyl)-N-(1,1,1-trifluoropropan-2-yl)-[1,2,4]triazolo[1,5-a]pyrimidin-7-amine, reverse-phase HPLC purification afforded the title compound. Yield: 62%. IR: ν 3411, 3207, 2923, 2853, 1638, 1616 cm$^{-1}$.

HRMS (ESI$^+$) calculated for $C_{20}H_{21}ClF_5N_6O_2$ [M+H$^+$]: 507.1335, found 507.1335.

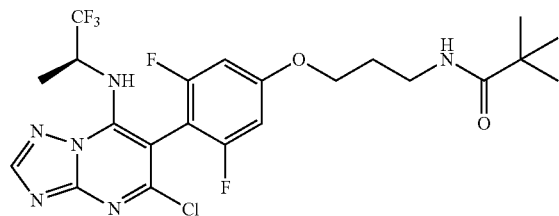 [SMILES: C[C@H](Nc1c(-c2c(F)cc(OCCCNC(=O)C(C)(C)C)cc2F)c(Cl)nc2ncnn12)C(F)(F)F]

(S)—N-(3-(4-(5-chloro-7-((1,1,1-trifluoropropan-2-yl)amino)-[1,2,4]Triazolo[1,5-a]pyrimidin-6-yl)-3,5-difluorophenoxy)propyl)pivalamide (CNDR-51595)

Following General Procedure B using N-(3-hydroxypropyl)pivalamide and (S)-5-chloro-6-(2,4,6-trifluorophenyl)-N-(1,1,1-trifluoropropan-2-yl)-[1,2,4]triazolo[1,5-c]pyrimidin-7-amine, reverse-phase HPLC purification afforded the title compound. Yield: 38%.

$^1$H-NMR (500 MHz; CDCl$_3$): δ 8.39 (s, 1H), 6.64 (m, 2H), 5.96 (m, 2H), 4.77 (broad s, 1H), 4.10 (t, J=5.9 Hz, 2H), 3.49 (q, J=6.3 Hz, 2H), 2.07 (m, 2H), 1.41 (d, J=6.8 Hz, 3H), 1.22 (s, 9H) ppm. HRMS (ESI$^+$) calculated for $C_{22}H_{25}N_6O_2F_5Cl$ [M+H$^+$]: 535.1642, found 535.1641.

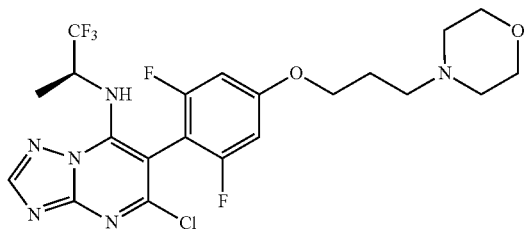 [SMILES: C[C@H](Nc1c(-c2c(F)cc(OCCCN3CCOCC3)cc2F)c(Cl)nc2ncnn12)C(F)(F)F]

(S)-5-Chloro-6-(2,6-difluoro-4-(3-morpholino-propoxyl)phenyl)-N-(1,1,1-trifluoropropan-2-yl)-[1,2,4]triazolo[1,5-a]pyrimidin-7-amine (CNDR-51596)

Following General Procedure B using 3-morpholinopropan-1-ol and (S)-5-chloro-6-(2,4,6-trifluorophenyl)-N-(1,1,1-trifluoropropan-2-yl)-[1,2,4]triazolo[1,5-a]pyrimidin-7-amine, reverse-phase HPLC purification afforded the title compound. Yield: 68%.

$^1$H-NMR (500 MHz; CDCl$_3$): δ 8.39 (s, 1H), 6.67-6.63 (m, 2H), 5.95 (d, J=10.5 Hz, 1H), 4.81 (broad s, 1H), 4.11 (t, J=6.1 Hz, 2H), 3.82 (t, J=4.7 Hz, 4H), 2.75 (m, 6H), 2.13 (m, 2H), 1.41 (d, J=6.8 Hz, 3H) ppm. IR: ν 3425, 2958, 2861, 2817, 1640, 1615, 1578 cm$^{-1}$. HRMS (ESI$^+$) calculated for $C_{21}H_{23}N_6O_2F_5Cl$ [M+H$^+$]: 521.1486, found 521.1488.

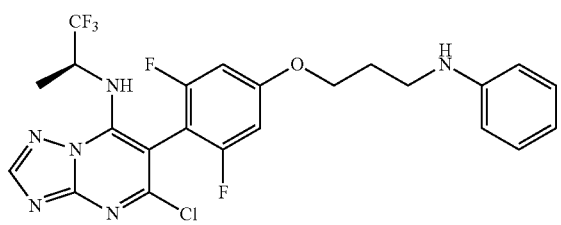 [SMILES: C[C@H](Nc1c(-c2c(F)cc(OCCCNc3ccccc3)cc2F)c(Cl)nc2ncnn12)C(F)(F)F]

(S)-5-Chloro-6-(2,6-difluoro-4-(3-(phenylamino)propoxy)phenyl)-N-(1,1,1-trifluoropropan-2-yl)-[1,2,4]triazolo[1,5-a]pyrimidin-7-amine (CNDR-51598)

Following General Procedure B using 3-(phenylamino)propan-1-ol and (S)-5-chloro-6-(2,4,6-trifluorophenyl)-N-(1,1,1-trifluoropropan-2-yl)-[1,2,4]triazolo[1,5-a]pyrimidin-7-amine, reverse-phase HPLC purification afforded the title compound. Yield: 53%.

$^1$H-NMR (500 MHz; CDCl$_3$): δ 8.40 (s, 1H), 7.20 (m, 2H), 6.73 (m, 1H), 6.67 (m, 4H), 5.89 (d, J=10.1 Hz, 1H), 4.77 (broad s, 1H), 4.16 (t, J=5.9 Hz, 2H), 3.40 (t, J=6.6 Hz, 2H), 2.17 (quintet, J=6.2 Hz, 2H), 1.41 (d, J=6.8 Hz, 3H) ppm. IR: ν 3338, 3209, 3113, 3055, 2950, 1614, 1575 cm$^{-1}$. HRMS (ESI$^+$) calculated for $C_{23}H_{21}N_6OF_5Cl$ [M+H$^+$]: 527.1380, found 527.1385.

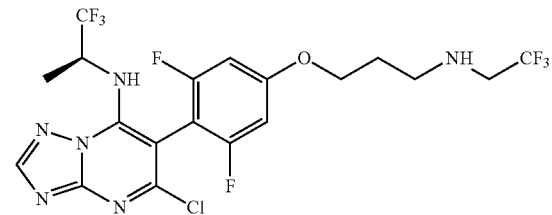 [SMILES: C[C@H](Nc1c(-c2c(F)cc(OCCCNCC(F)(F)F)cc2F)c(Cl)nc2ncnn12)C(F)(F)F]

(S)-5-chloro-6-(2,6-difluoro-4-(3-((2,2,2-trifluoroethyl)amino)propoxy)phenyl)-N-(1,1,1-trifluoropropan-2-yl)-[1,2,4]triazolo[1,5-a]pyrimidin-7-amine (CNDR-51599)

Following General Procedure B using 3-((2,2,2-trifluoroethyl)amino)propan-1-ol and (S)-5-chloro-6-(2,4,6-trifluorophenyl)-N-(1,1,1-trifluoropropan-2-yl)-[1,2,4]triazolo[1, 5-a]pyrimidin-7-amine, reverse-phase HPLC purification afforded the title compound. Yield: 89%.

$^1$H-NMR (500 MHz; CDCl$_3$): δ 8.40 (s, 1H), 6.69-6.65 (m, 2H), 5.92 (d, J=10.3 Hz, 1H), 4.77 (broad s, 1H), 4.15 (t, J=6.1 Hz, 2H), 3.25 (q, J=9.4 Hz, 2H), 2.99 (t, J=6.7 Hz, 2H), 2.04 (quintet, J=6.4 Hz, 2H), 1.42 (d, J=6.8 Hz, 3H). HRMS (ESI$^+$) calculated for C$_{19}$H$_{18}$ClF$_8$N$_6$O [M+H$^+$]: 533.1103, found 533.1199.

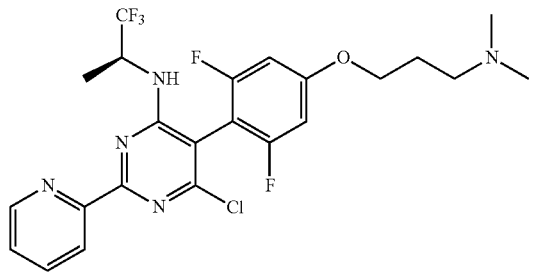 [SMILES: C[C@H](Nc1nc(-c2ccccn2)nc(Cl)c1-c1c(F)cc(OCCCN(C)C)cc1F)C(F)(F)F]

(S)-6-Chloro-5-(4-(3-(dimethylamino)propoxy)-2,6-difluorophenyl)-2-(pyridin-2-yl)-N-(1,1,1-trifluoropropan-2-yl)pyrimidin-4-amine (CNDR-51561)

Prepared as CNDR-51554 from (S)-6-chloro-2-(pyridin-2-yl)-5-(2,4,6-trifluorophenyl)-N-(1,1,1-trifluoropropan-2-yl)pyrimidin-4-amine (CNDR-51552) and 3-(dimethylamino)propan-1-ol. Yield: 7%.

HRMS [ESI]$^+$: calculated for C$_{23}$H$_{24}$ClF$_5$N$_5$O: 516.1590; found: 516.1592.

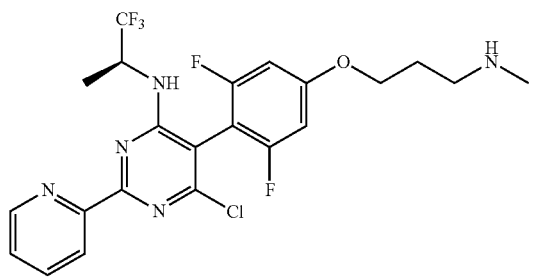 [SMILES: CNCCCOc1cc(F)c(-c2c(Cl)nc(-c3ccccn3)nc2N[C@@H](C)C(F)(F)F)c(F)c1]

(S)-6-Chloro-5-(2,6-difluoro-4-(3-(methylamino)propoxy)phenyl)-2-(pyridin-2-yl)-N-(1,1,1-trifluoropropan-2-yl)pyrimidin-4-amine (CNDR-51562)

Prepared as CNDR-51554 from (S)-6-chloro-2-(pyridin-2-yl)-5-(2,4,6-trifluorophenyl)-N-(1,1,1-trifluoropropan-2-yl)pyrimidin-4-amine (CNDR-51552) and 3-(methylamino)propan-1-ol. Yield: 10%

$^1$H-NMR (500 MHz; MeOD): δ 8.84 (m, 2H), 8.51-8.48 (m, 1H), 7.98 (t, J=6.5 Hz, 1H), 6.83 (m, 2H), 5.66 (m, 1H), 4.21 (t, J=5.7 Hz, 2H), 3.25 (t, J=7.4 Hz, 2H), 2.77 (s, 3H), 2.23 (m, 2H), 1.42 (d, J=7.0 Hz, 3H).

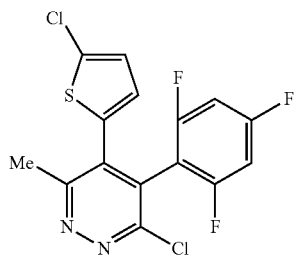 [SMILES: Cc1nnc(Cl)c(-c2c(F)cc(F)cc2F)c1-c1ccc(Cl)s1]

3-Chloro-5-(5-chlorothiophen-2-yl)-6-methyl-4-(2,4,6-trifluorophenyl)pyridazine (CNDR-51566)

The title compound was prepared as described in Lamberth et al., Bioorg. Med. Chem. 2012, 20, 2803. The spectral data were identical to that reported in the literature.

$^1$H-NMR (500 MHz; CDCl$_3$): δ 6.83 (d, J=3.8 Hz, 1H), 6.73-6.70 (m, 3H), 2.71 (s, 3H) ppm.

MS (ESI$^+$) 374.97 [M+H$^+$].

Microtubule Stabilization Assay

The HEK293 cell subclone, QBI293, was maintained in DMEM supplemented with 10% fetal calf or bovine serum, 1% penicillin/streptomycin antibiotic solution and 1% glutamine at 37° C. in 5% CO$_2$. Cells were plated into 6-well plates at a density of 800,000 cells/well. Each plate had a well that contained the known microtubule stabilizer, epothilone D or cevipabulin, as a positive control and the remaining wells were used for compound evaluation. Test compounds were added at multiple concentrations to the test wells and incubated for 4 h. Subsequently, the media was removed and the cells were washed with 1 ml of ice-cold phosphate-buffered saline (PBS). After removal of PBS, 0.2 ml of ice-cold RIPA (0.5% sodium deoxycholate, 0.1% SDS, 1% NP-40, 5 mM EDTA, pH 8.0) containing protease inhibitor mix (1 μg/ml each of pepstatin, leupeptin, TLCK, TPCK and trypsin inhibitor), 1 mM PMSF and 1 μM trichostatin A was added to the wells. The wells were then scraped using a cell scraper and pipetted into 1.5 ml microfuge tubes. The tubes were sonicated with a handheld sonicator at 20× on a power setting of 2, followed by centrifugation for 30 min at 15,000 rpm at 4° C. Supernatants were removed and quantified for protein concentration and the acetyl-tubulin levels were determined using an ELISA as described.

Acetyl-Tubulin ELISA 384-well plates were coated with 12G10α-tubulin antibody (Developmental Studies Hybridoma Bank at the University of Iowa; 10 μg/ml) in 30 μl of cold 0.1 M bicarbonate buffer. After overnight incubation at 4° C., the plates were washed with cold PBS, followed by the addition of Block-Ace solution and overnight incubation at 4° C. The blocking solution was removed and 10 μl of EC buffer (0.02 M sodium phosphate, pH 7.0, 2 mM EDTA, 0.4 M NaCl, 0.2% bovine serum albumin, 0.05% CHAPS, 0.4% BlockAce and 0.05% NaN$_3$) was added to each well. Cell culture supernatants were diluted in EC buffer to final protein concentrations of 9, 3, 1.5 and 0.5 μg/30 μl, and 30 μl of each were added to wells in duplicate and plates were subsequently sealed. After overnight incubation at 4° C., the plates were aspirated and washed with cold PBS containing 0.05% Tween-20 and 0.05% thimerisol (PBS-Tween buffer), followed by addition of 30 μl/well of HRP-conjugated acetyl-tubulin antibody (6-11B-1 antibody from Sigma-Aldrich) that was prepared with a Peroxidase Labeling Kit following the manufacturer's instructions that was subsequently diluted 1:1000 in C buffer (0.02 M sodium phosphate, pH 7.0, 2 mM EDTA, 0.4 M NaCl, 1% bovine serum albumin and 0.05% thimerisol). The plates were incubated at room temperature for 4 h on a platform rocker, followed by washing with cold PBS-Tween buffer. Peroxidase substrate solution (30 µl) was added and the reaction was quenched after 5-10 min by addition of 30 µl of 10% phosphoric acid. Plates were read on a SpectraMax M5 plate reader at 450 nm. Because an acetyl-tubulin standard is not available, all data were normalized to a control treatment condition (e.g., no compound addition).

Results for preferred compounds of the invention are depicted in FIGS. 1-12 and Tables 5 and 6.

Acetyl Tubulin Immunofluorescence

The HEK293 cell subclone, QBI293, was plated onto poly-D-lysine-coated glass coverslips at 50,000 cells/ml in DMEM supplemented with 10% fetal calf or bovine serum, 1% penicillin/streptomycin antibiotic solution and 1% glutamine and maintained overnight at 37° C. in 5% $CO_2$. The next day, cells were left untreated or were treated with 100 nM epothilone D, 100 nM CNDR-51533 or 1 µM colchicine. After an additional 4 h of incubation at 37° C. in 5% $CO_2$, cells were washed twice with PBS, and then fixed for 15 min in PBS containing 4% paraformaldehyde. The cells were again washed twice with PBS, and permeabilized with 0.1% Triton X-100 in PBS for 15 min. Following the Triton X-100 treatment, the cells were washed twice in PBS, and treated with PBS containing 3% bovine serum albumin for 1 h. Acetyl-tubulin antibody was subsequently added (1:1000 dilution) and incubated for 1 h. Cells were then washed cells 3×5 min with 0.1% Triton X-100 in PBS, and secondary antibody (goat-anti-mouse labeled with Alexa fluor 488 at 1:1000) was added and allowed to incubate for 1 h. Upon completion of the antibody incubation, cells were washed 2×5 min with 0.1% Triton X-100 in PBS, followed by 15 min incubation with PBS containing DAPI (1:12000). Finally, the cells were washed once with PBS, followed by H2O, and the cover slips were mounted onto slides with Fluoromount G. Images were acquired on a microscope equipped for fluorescence detection. Each treatment was tested on three separate coverslips.

Determination of Plasma and Brain Compound Concentrations

Mouse brains were homogenized in 10 mM ammonium acetate, pH 5.7 (1:2; w/v) using a handheld sonic homogenizer. Mouse plasma was obtained from blood that was collected into a 1.5 ml tube containing 0.5M EDTA solution and which was centrifuged for 10 minutes at 4500 g at 4° C. Aliquots (50 µl) of brain homogenates (50% w/v in 100 mM NH4OAC pH 5.75) or plasma were mixed with 0.2 ml of acetonitrile, centrifuged at 15,000 g, and the resulting supernatant was used for subsequent LC-MS/MS analysis. The LC-MS/MS system was comprised of an Aquity UPLC and a TQ MS that was controlled using MassLynx software (Waters Corporation, Milford, Mass., USA). Compounds were detected using multiple reaction monitoring (MRM) of their specific collision-induced ion transitions. Samples were separated on an Aquity BEH C18 column (1.7 µm, 2.1×50 mm) at 35° C. Operation was in positive electrospray ionization mode, with mobile phase A of 0.1% (v/v) formic acid, and B of acetonitrile with 0.1% (v/v) formic acid. Injections of 5 µl were separated at a flow rate of 0.6 mL/min using a gradient from 5% to 95% B over two minutes, followed by wash and re-equilibration steps. The MS was operated with a desolvation temperature of 450° C. and a source temperature of 150° C. Desolvation and source nitrogen gas flows were 900 L/hr and 50 L/hr, respectively. Source and MS/MS voltages were optimized for each compound using the MassLynx auto tune utility. To account for possible matrix effects on analytes, standard curves were generated for each compound from brain homogenate and plasma samples that had compound added at 24, 240, 2400 and 24000 nM. The standard curve samples were extracted and analyzed in an identical fashion as the corresponding tissue-derived samples, and peak areas were plotted against concentration and a linear regression curve was used to obtain estimated concentrations of the tissue-derived samples using the peak areas. In all cases, the tissue-derived sample peak areas fell within the linear portion of standard curves that were prepared and analyzed concurrently with the samples.

Determination of Brain Acetyl-Tubulin Levels

CD1 mice were administered vehicle (DMSO) or CNDR-51549 at multiple doses once per day for 3 days. Whole brain hemispheres were obtained from the mice, which were euthanized using protocols approved by the University of Pennsylvania Institutional Animal Care and Use Committee, and were homogenized and then briefly sonicated with a handheld sonicator in 1:5 (w/v) RIPA-INH buffer. The homogenates were centrifuged at 100,000×g for 30 min at 4° C., and the supernatants were collected. The supernatant samples were diluted before protein determination with a BCA assay. These supernatant samples were utilized in the Acetyl-Tubulin ELISA, as described above.

References

Ballatore, C., Lee, V. M. Y., & Trojanowski, J. Q. Tau-mediated neurodegeneration in Alzheimer's disease and related disorders. *Nat. Rev. Neurosci.* 8, 663-672 (2007).

Buee, L., Bussiere, T., Buee-Scherrer, V., Delacourte, A., & Hof, P. R. Tau protein isoforms, phosphorylation and role in neurodegenerative disorders. *Brain Research Reviews* 33, 95-130 (2000).

Roy, S., Zhang, B., Lee, V. M. Y., & Trojanowski, J. Q. Axonal transport defects: a common theme in neurodegenerative diseases. *Acta Neuropathol. (Berl).* 109, 5-13 (2005).

Brunden, K. R. et al. Epothilone D improves microtubule density, axonal integrity and cognition in a transgenic mouse model of tauopathy. *J. Neurosci.* 30, 13861-13866 (2010).

Zhang, B. et al. Microtubule-binding drugs offset tau sequestration by stabilizing microtubules and reversing fast axonal transport deficits in a tauopathy model. *Proc. Natl. Acad. Sci. U.S.A.* 102, 227-231 (2005).

Zhang, B. et al. The microtubule-stabilizing agent, epothilone D, reduces axonal dysfunction, cognitive deficits, neurotoxicity and Alzheimer-like pathology in an interventional study with aged tau transgenic mice. *J. Neurosci.* 32, 3601-3611 (2012).

Brunden, K. R. et al. The characterization of microtubule-stabilizing drugs as possible therapeutic agents for Alzheimer's disease and related tauopathies. *Pharmacol. Res.* 63, 341-351 (2011).

Zhang, N. et al. Synthesis and SAR of [1,2,4]triazolo[1,5-a]pyrimidines, a class of anticancer agents with a unique mechanism of tubulin inhibition. *J Med Chem* 50, 319-327 (2007).

Zhang, N. et al. Synthesis and SAR of 6-chloro-4-fluoroalkylamino-2-heteroaryl-5-(substituted)phenylpyrimidines as anti-cancer agents. *Bioorg. Med Chem* 17, 111-118 (2009).

Crowley, P. J. et al. Synthesis and fungicidal activity of tubulin polymerisation promoters. Part 1: pyrido[2,3-b]pyrazines. *Pest. Manag. Sci.* 66, 178-185 (2010).

Crowley, P. J. et al. Neimentowski-type synthesis of pyrido[3,2-e][1,2,4]trazines: potent aza-analogs of pyrido[2,3-b]pyrazine fungicides. *Tetrahedron Lett.* 51, 2652-2654 (2010).

Lamberth, C. et al. Synthesis and fungicidal activity of tubulin polymerisation promoters. Part 2: Pyridazines. *Bioorg. Med Chem* 20, 2803-2810 (2012)

Pees, K.-J.; Albert, G. Patent U.S. Pat. No. 6,117,876, 2000.

Wu, Y.; Schmid, J.; Afragola, J. T.; Blum, D.; Ayral-Kaloustian, S. Patent US 2005/0124635 A1, 2005.

Zhang, N.; Ayral-Kaloustian, S.; Nguyen, T.; Afragola, J.; Hernandez, R.; Lucas, J.; Gibbons, J.; Beyer, C. J. Med. Chem. 2007, 50, 319-327.

Pfrengle, W.; Pees, K.-J.; Albert, G.; Carter, P.; Rehnig, A.; Cotter, H. V. T. Patent U.S. Pat. No. 5,986,135, 1999.

Zhang et al, Synthesis and SAR of 6-chloro-4-fluoroalkylamino-2-heteroaryl-5-(substituted)phenylpyrimidines as anti-cancer agents, Bioorganic & Medicinal Chemistry 17 (2009) 111-118.

Lamberth et al Synthesis and fungicidal activity of tubulin polymerization promoters Part 2 pyridazines Bioorganic & Medicinal Chemistry 20 2012 2803-2810.

What is claimed:

1. A method of treating a neurodegenerative disease in a patient in need thereof comprising administering to the patient a therapeutically effective amount of a compound of formula II:

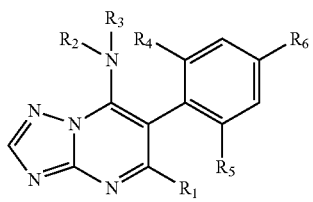

wherein
$R_1$ is H, Cl, F, or Br;
$R_2$ is $C_{1-6}$alkyl or substituted $C_{1-6}$alkyl;
$R_3$ is H; or $R_2$ and $R_3$, together with the N atom to which they are attached, form a heterocyclo$C_{3-6}$alkyl;
$R_4$ is H, Cl, F, or Br;
$R_5$ is H, Cl, F, or Br;
$R_6$ is F, Cl, Br, $-N_3$, $-OC_{1-6}$alkyl, $-OC_{1-6}$alkyleneOH, $-OC_{1-6}$alkylene-halo,
$-OC_{1-6}$alkyleneNR$_7$R$_8$, $-OC_{1-6}$substituted-alkyleneNR$_7$R$_8$, or
$-OC_{3-6}$cycloalkyleneNR$_7$R$_8$, wherein R$_7$ and R$_8$ are each independently H,
$C_{1-6}$alkyl, substituted $C_{1-6}$alkyl, $-C(O)C_{1-6}$alkyl, or aryl; or R$_7$ and R$_8$ together form a heterocyclic ring;
or a stereochemical isomer thereof;
or a pharmaceutically acceptable salt thereof.

2. The method of claim 1, wherein $R_1$ is Cl.
3. The method of claim 1, wherein $R_2$ is $C_{1-6}$alkyl.
4. The method of claim 3, wherein $R_2$ is methyl, ethyl, propyl, or isopropyl.
5. The method of claim 1, wherein $R_2$ is substituted $C_{1-6}$alkyl.
6. The method of claim 5, wherein $R_2$ is $-CH(CH_3)(CF_3)$.
7. The method of claim 5, wherein $R_2$ is $-CH_2(CF_3)$.
8. The method of claim 1, wherein $R_3$ is H.
9. The method of claim 1, wherein $R_4$ is F.
10. The method of claim 1, wherein $R_5$ is F.
11. The method of claim 1, wherein $R_3$, $R_4$, and $R_5$ are each F.
12. The method of claim 1, wherein $R_6$ is F.
13. The method of claim 1, wherein $R_6$ is $-OC_{1-6}$alkyleneNR$_7$R$_8$.
14. The method of claim 13, wherein $R_6$ is $-O-CH_2CH_2CH_2-N(CH_3)_2$ or $-O-CH_2CH_2CH_2-NH(CH_3)$.
15. The method of claim 1, wherein $R_6$ is $OC_{1-6}$cycloalkyleneNR$_7$R$_8$.
16. The method of claim 15, wherein $R_6$ is

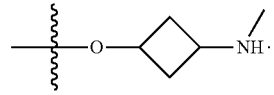 [SMILES: *OC1CC(NC)C1 ; "."]

17. The method of claim 1, wherein $R_6$ is $-OC_{1-6}$alkyl.
18. The method of claim 1, wherein $R_6$ is $-OC_{1-6}$alkyleneOH.
19. The method of claim 1, wherein $R_6$ is $-OC_{1-6}$alkylene-halo.
20. The method of claim 1, wherein $R_6$ is $-OC_{1-6}$substituted-alkyleneNR$_7$R$_8$.
21. The method of claim 20, wherein $R_7$ is H.
22. The method of claim 20, wherein $R_8$ is $C_{1-6}$alkyl.
23. The method of claim 20, wherein $R_8$ is substituted $C_{1-6}$alkyl.
24. The method of claim 23, wherein the alkyl is substituted with $CF_3$.
25. The method of claim 20, wherein $R_8$ is $-C(O)C_{1-6}$alkyl.
26. The method of claim 20, wherein $R_8$ is aryl.
27. The method of claim 1, wherein the compound of formula II is

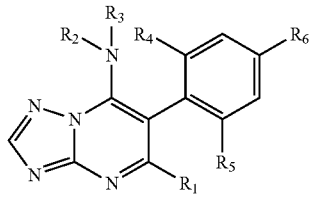

| $R_1$ | $R_2$ | $R_3$ | $R_4$ | $R_5$ | $R_6$ |
|---|---|---|---|---|---|
| Cl | H | H | F | F | F |
| Cl | $-CH(CH_3)CF_3$ (S) | H | F | F | F |
| Cl | $-CH(CH_3)CF_3$ (R) | H | F | F | F |
| Cl | $-CH(CH_3)CF_3$ (S,R) | H | F | F | F |
| Cl | $-CH(CH_3)CF_3$ (S) | H | F | F | $-OCH_2CH_2CH_2NHCH_3$ |

-continued

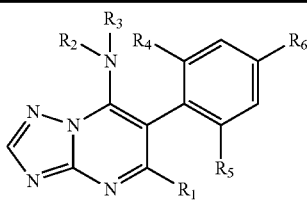

| R₁ | R₂ | R₃ | R₄ | R₅ | R₆ |
|---|---|---|---|---|---|
| Cl | —CH(CH₃)CF₃ (R) | H | F | F | —OCH₂CH₂CH₂NHCH₃ |
| Cl | —CH(CH₃)CF₃ (S,R) | H | F | F | —OCH₂CH₂CH₂NHCH₃ |
| Cl | H | H | F | F | —OCH₂CH₂CH₂NHCH₃ |
| Cl | —CH(CH₃)CF₃ (S) | H | F | F | —OCH₂CH₂CH₂N(CH₃)₂ |
| Cl | —CH(CH₃)CF₃ (R) | H | F | F | —OCH₂CH₂CH₂N(CH₃)₂ |
| Cl | —CH(CH₃)CF₃ (S,R) | H | F | F | —OCH₂CH₂CH₂N(CH₃)₂ |
| Cl | —CH(CH₃)CF₃ (S) | H | F | F | -O-cyclobutyl-NHCH₃ |
| Cl | —CH(CH₃)CF₃ (R) | H | F | F | -O-cyclobutyl-NHCH₃ |
| Cl | —CH(CH₃)CF₃ (S,R) | H | F | F | -O-cyclobutyl-NHCH₃ |
| Cl | —CH(CH₃)CF₃ (S) | H | F | F | -OCH₂CH₂CH₂-pyrrolidine |
| Cl | —CH(CH₃)CF₃ (S) | H | F | F | -OCH₂CH₂CH₂OH |
| Cl | —CH(CH₃)CF₃ (S) | H | F | F | -OCH₂CH₂CH₂NH₂ |
| Cl | —CH(CH₃)CF₃ (S) | H | F | F | -OCH₂CH₂-(3-amino-oxetane) |
| Cl | —CH(CH₃)CF₃ (S) | H | F | F | -OCH₂CH₂CH₂F |
| Cl | —CH(CH₃)CF₃ (S) | H | F | F | -OCH₂CH₂CH₂Cl |
| Cl | —CH(CH₃)CF₃ (S) | H | F | F | -OCH₂CH₂CH₂NHC(O)CH₃ |
| Cl | —CH(CH₃)CF₃ (S) | H | F | F | -OCH₂CH₂CH₂N(CH₃)C(O)CH₃ |

-continued

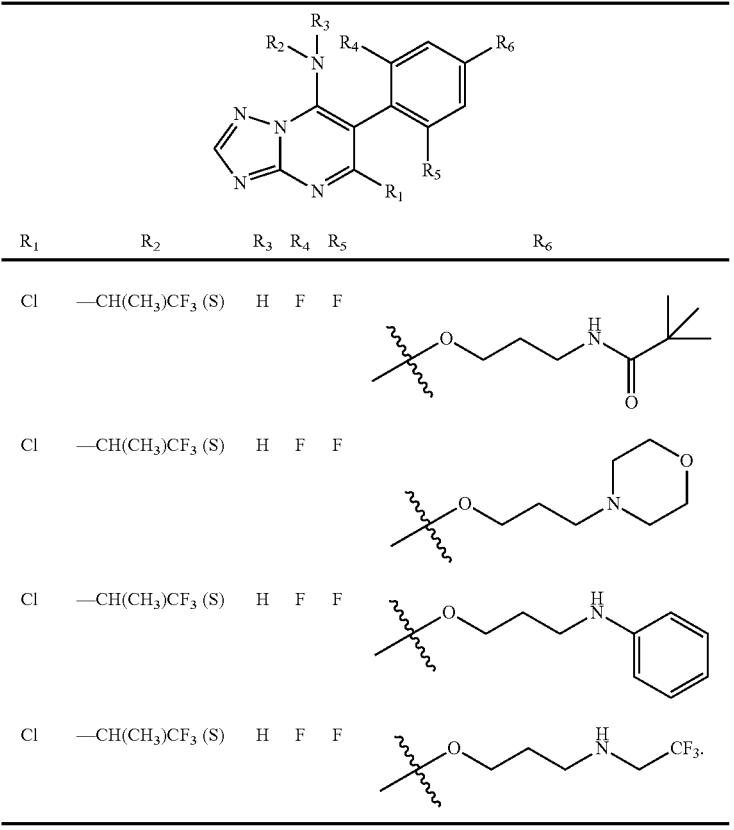

| R₁ | R₂ | R₃ | R₄ | R₅ | R₆ |
|---|---|---|---|---|---|
| Cl | —CH(CH₃)CF₃ (S) | H | F | F | |
| Cl | —CH(CH₃)CF₃ (S) | H | F | F | |
| Cl | —CH(CH₃)CF₃ (S) | H | F | F | |
| Cl | —CH(CH₃)CF₃ (S) | H | F | F | |

28. The method of claim 1, wherein the neurodegenerative disease is characterized by a tauopathy or compromised microtubule function in the brain of the patient.

29. The method of claim 1, wherein the neurodegenerative disease is Alzheimer's disease, frontotemporal lobar degeneration, Pick's disease, progressive supranuclear palsy (PSP), corticobasal degeneration, Parkinson's disease (PD), PD with dementia, Lewy body disease with dementia, or amyotrophic lateral sclerosis.

30. The method of claim 1, wherein the neurodegenerative disease is traumatic brain injury or post traumatic stress disorder.

31. The method of claim 1, wherein the neurodegenerative disease is schizophrenia.

32. The method of claim 30, wherein the traumatic brain injury is repetitive traumatic brain injury or chronic traumatic encephalopathy.

* * * * *

UNITED STATES PATENT AND TRADEMARK OFFICE
CERTIFICATE OF CORRECTION

PATENT NO. : 9,649,317 B2
APPLICATION NO. : 14/429101
DATED : May 16, 2017
INVENTOR(S) : Carlo Ballatore et al.

Page 1 of 1

It is certified that error appears in the above-identified patent and that said Letters Patent is hereby corrected as shown below:

In the Specification

Column 1,
Lines 16-19, delete the entire Paragraph after the heading "Government Rights":
"This invention was made with government support under grant numbers R01 AG44332 and AG0344140 awarded by the National Institutes of Health. The government has certain rights in the invention"

And insert therefor:
-- This invention was made with government support under AG034140 and AG044332 awarded by the National Institutes of Health. The government has certain rights in the invention. --.

Signed and Sealed this
Twenty-eighth Day of December, 2021

Drew Hirshfeld
*Performing the Functions and Duties of the*
*Under Secretary of Commerce for Intellectual Property and*
*Director of the United States Patent and Trademark Office*